(12) United States Patent
Akeroyd et al.

(10) Patent No.: US 12,303,855 B2
(45) Date of Patent: May 20, 2025

(54) STABLE POLYUREA MICROCAPSULE COMPOSITIONS FOR ALDEHYDE FRAGRANCES

(71) Applicant: INTERNATIONAL FLAVORS & FRAGRANCES INC., New York, NY (US)

(72) Inventors: Niels Akeroyd, Bilthoven (NL); Laura French, Hoboken, NJ (US); Robert Allan Hunter, Ankeveen (NL); Yabin Lei, Holmdel, NJ (US); Lewis Michael Popplewell, Morganville, NJ (US); Volkert De Villeneuve, Voorburg (NL); Clementine Marteau-Roussy, Vincennes (FR)

(73) Assignee: INTERNATIONAL FLAVORS & FRAGRANCES INC., New York, NY (US)

( * ) Notice: Subject to any disclaimer, the term of this patent is extended or adjusted under 35 U.S.C. 154(b) by 1121 days.

(21) Appl. No.: 17/050,855

(22) PCT Filed: Apr. 26, 2019

(86) PCT No.: PCT/US2019/029279
§ 371 (c)(1),
(2) Date: Oct. 27, 2020

(87) PCT Pub. No.: WO2019/210125
PCT Pub. Date: Oct. 31, 2019

(65) Prior Publication Data
US 2021/0237021 A1  Aug. 5, 2021

Related U.S. Application Data

(60) Provisional application No. 62/663,714, filed on Apr. 27, 2018.

(51) Int. Cl.
| | | |
|---|---|---|
| C11D 3/50 | (2006.01) |
| A61K 8/11 | (2006.01) |
| A61K 8/33 | (2006.01) |
| A61K 8/87 | (2006.01) |
| A61Q 5/02 | (2006.01) |
| A61Q 5/12 | (2006.01) |
| B01J 13/16 | (2006.01) |
| C08G 18/32 | (2006.01) |
| C08G 18/64 | (2006.01) |
| C08G 18/76 | (2006.01) |
| C08G 18/78 | (2006.01) |
| C08G 18/79 | (2006.01) |
| C08G 18/80 | (2006.01) |
| C08L 75/02 | (2006.01) |
| C11B 9/00 | (2006.01) |
| C11D 3/00 | (2006.01) |
| D06M 13/00 | (2006.01) |
| D06M 23/12 | (2006.01) |

(52) U.S. Cl.
CPC ............. *B01J 13/16* (2013.01); *A61K 8/11* (2013.01); *A61K 8/33* (2013.01); *A61K 8/87* (2013.01); *A61Q 5/02* (2013.01); *A61Q 5/12* (2013.01); *C08G 18/3228* (2013.01); *C08G 18/6423* (2013.01); *C08G 18/6446* (2013.01); *C08G 18/7664* (2013.01); *C08G 18/7831* (2013.01); *C08G 18/794* (2013.01); *C08G 18/8029* (2013.01); *C08L 75/02* (2013.01); *C11B 9/00* (2013.01); *C11D 3/001* (2013.01); *C11D 3/505* (2013.01); *D06M 13/005* (2013.01); *D06M 23/12* (2013.01); *D06M 2200/50* (2013.01)

(58) Field of Classification Search
CPC ........... C11D 3/505; C11D 3/50; C11D 3/502; C11D 7/264; C11D 7/3236; C11D 9/44; C11D 9/442; C11D 17/0039; C11D 2111/12
See application file for complete search history.

(56) References Cited

U.S. PATENT DOCUMENTS

| | | | |
|---|---|---|---|
| 10,894,007 B2 * | 1/2021 | Conway | A61K 8/37 |
| 2013/0330292 A1 | 12/2013 | Lei et al. | |
| 2014/0044761 A1 | 2/2014 | Lei et al. | |
| 2014/0323376 A1 | 10/2014 | Berthier et al. | |
| 2016/0193122 A1 | 7/2016 | Lei et al. | |
| 2017/0121649 A1 | 5/2017 | Shi et al. | |
| 2017/0204223 A1 * | 7/2017 | Veliath | C11D 3/0068 |
| 2017/0252274 A1 * | 9/2017 | Lei | A61K 8/84 |
| 2018/0042825 A1 * | 2/2018 | Lei | A01N 25/28 |
| 2018/0064615 A1 * | 3/2018 | Brahms | A61K 9/06 |
| 2018/0085291 A1 * | 3/2018 | Sasaki | C11D 17/06 |
| 2018/0154328 A1 * | 6/2018 | Ferguson | C11D 3/222 |

FOREIGN PATENT DOCUMENTS

| | | |
|---|---|---|
| WO | 2011161265 A2 | 12/2011 |
| WO | 2016071149 A1 | 5/2016 |
| WO | 2018019894 A1 | 2/2018 |
| WO | 2018019896 A1 | 2/2018 |
| WO | 2018019908 A1 | 2/2018 |

OTHER PUBLICATIONS

International Search Report, PCT Application No. PCT/US2019/029279, dated Aug. 7, 2019, 5 pgs.

* cited by examiner

Primary Examiner — Charles I Boyer

(57) ABSTRACT

Stable polyurea microcapsule compositions suitable for encapsulating aldehydes with a low viscosity. Also disclosed are consumer products containing such a composition and its preparation methods.

21 Claims, No Drawings

STABLE POLYUREA MICROCAPSULE COMPOSITIONS FOR ALDEHYDE FRAGRANCES

BACKGROUND

Microencapsulation is used in a variety of applications where there is a need to deliver, apply, or release an active material including a fragrance, flavor, and malodor counteraction agent to a target area in a time-delayed or controlled manner.

Microcapsules with a polyurea capsule wall were developed to encapsulate flavors and fragrances in consumer products. See US 2013/0330292 A1 and US 2016/0193122 A1. The polyurea capsule wall is formed in an interfacial polymerization between a polyisocyanate and a polyamine.

Polyurea microcapsules are inefficient in encapsulating aldehyde fragrance ingredients. See WO 2016/071149 A1. Polyurea capsules with a high level of aldehydes tend to aggregate and increase the viscosity of the capsule slurry to a point rendering them unsuitable for use. It is believed that aldehyde fragrance ingredients react with polyamine during the polymerization, resulting in aggregation, low capsule loading and decreased stability. To address this issue, WO 2011/161265 A1 describes a method of converting aldehydes to precursors before encapsulation. The additional conversion step not only increases the cost and complexity, but also limits the use of aldehydes. Not all aldehydes can be converted to precursors.

WO 2016/071149 A1 proposed a different approach to encapsulate aldehydes at a level up to 6% by weight of the encapsulated fragrance. Alkyl salicylates, as well as a 2,2, 2-trisubstituted acetal, must be used together with aldehydes. Including a salicylate and acetal is not desirable in many consumer products. Salicylate intolerance in many people causes itchy skin, asthma reactions, or other symptoms.

Other publications described methods that do not utilize polyamine as the starting material for the microcapsules. See WO 2018/019908, WO 2018/019894, and WO 2018/019896. These microcapsules are less stable in certain consumer products.

There is a need to develop stable, aldehyde-containing microcapsules for use in laundry, washing, cleaning, surface care, personal care, and skin care.

SUMMARY OF THE INVENTION

This invention is based on the discovery of processes that encapsulate a high content of aldehydes in a microcapsule core. The microcapsule compositions thus prepared are particularly suitable for fabric care products as many aldehydes are essential to promote the clean and fresh sensation in fabric care products.

One aspect of this invention relates to microcapsule compositions comprising a plurality of microcapsules dispersed in an aqueous phase. Each microcapsule having a microcapsule core and a microcapsule wall encapsulating the microcapsule core. The microcapsule core contains a fragrance having 8% to 100% one or more aldehydes by weight of the fragrance. The microcapsule wall is formed of an encapsulating polymer. The encapsulating polymer contains a polyurea polymer that is a reaction product of a multi-functional electrophile and a multi-functional nucleophile. The multi-functional electrophile contains a polyisocyanate. The multi-functional nucleophile contains a polyamine. The microcapsule composition has a viscosity of 2000 centipoises or less at a shear rate of 21 hertz and a temperature of 25° C. Each microcapsule composition contains by weight (i) 5% to 80% of the fragrance, and (ii) 0.1% to 15% of the encapsulating polymer.

Typically, the microcapsule composition contains a dispersant at a level of 0.1% to 10% by weight of the composition. Exemplary dispersants include a polyvinyl alcohol, polystyrene sulfonate, carboxymethyl cellulose, naphthalene sulfonate condensate salt, polyvinylpyrrolidone, or copolymer of vinyl pyrrolidone and quaternized dimethylaminoethyl methacrylate.

The microcapsule composition preferably comprises a water-soluble organic or inorganic salt of an alkali metal or alkaline earth metal at least 0.01% by weight of the composition.

In some embodiments, the microcapsule composition contains a deposition aid selected from the group consisting of polyquaternium-4, polyquaternium-5, polyquaternium-6, polyquaternium-7, polyquaternium-10, polyquaternium-11, polyquaternium-16, polyquaternium-22, polyquaternium-24, polyquaternium-28, polyquaternium-37, polyquaternium-39, polyquaternium-44, polyquaternium-46, polyquaternium-47, polyquaternium-53, polyquaternium-55, polyquaternium-67, polyquaternium-68, polyquaternium-69, polyquaternium-73, polyquaternium-74, polyquaternium-77, polyquaternium-78, polyquaternium-79, polyquaternium-79/hydrolyzed keratin, polyquaternium-80, polyquaternium-81, polyquaternium-82, polyquaternium-86, polyquaternium-88, polyquaternium-101, polyvinylamine, polyethyleneimine, a copolymer of vinylamine and vinylformamide, methacrylamidopropyl trimethyl ammonium polymer, polyacrylamide, polyacrylic acid, dimethyl ammonium polymer, polyvinylformamide, polyvinylpyrrolidone, polyvinylalcohol, a copolymer of acrylamide and 3-methacryloylaminopropyl trimethylammonium, a 3-acrylamidopropyl trimethylammonium polymer or its copolymer, a diallyldimethylammoniumchloride polymer and its copolymer, a polysaccharide with saccharide unit functionalized with hydroxypropyl trimmonium, ethyltrimonium chloride methacrylate/hydrolyzed wheat protein copolymer, alkyl-monium hydroxypropyl hydrolyzed protein, xlylose, galactose, hydroxypropylated glucose, hydroxyethylated glucose, hydroxymethylated glucose, functionalized branched polyethylenimine, caprolactone, catechol, hydroxypropylcellulose, polymer comprising units derived from polyethylene glycol and terephthalate, and combinations thereof.

Further, the microcapsule composition can also contain a rheology modifier, a core modifier, or both.

Another aspect of this invention relates to methods of preparing any microcapsule compositions above. One method include the steps of (a) providing an oil-in-water emulsion containing (i) an aqueous phase having a microcapsule formation aid, a polyamine, a water-soluble inorganic or organic salt of an alkali or alkaline earth metal, and water, and (ii) an oil phase having the fragrance and the polyisocyanate; (b) causing the formation of a microcapsule precursor having a microcapsule core that contains the fragrance and a microcapsule wall formed of reaction product of the polyisocyanate and polyamine, and (c) curing the microcapsule precursor to obtain a microcapsule composition of this invention.

Also within the scope of this invention is a consumer product containing one of the microcapsule compositions. The consumer product can be a baby care product, a diaper rash cream or balm, a baby powder, a diaper, a bib, a baby wipe, a cosmetic preparation, a powder foundation, a liquid foundation, an eye shadow, a lipstick or lip balm, a home care product, an all-purpose cleaner, a bathroom cleaner, a floor cleaner, a window cleaner, a plastics polish, a bleach, a toilet cleaner, a toilet rimblock, a bath tissue, a paper towel, a disposable wipe, liquid air freshener, air freshener spray, a spray dispenser product, an incense stick, a rug deodorizer, a candle, a room deodorizer, a liquid dish detergent, an automatic dish detergent, a powder dish detergent, a leather detergent, a tablet dish detergent, a paste dish detergent, a unit dose tablet or capsule, a flavor, a beverage flavor, a diary flavor, a fruit flavor, a miscellaneous flavor, a sweet goods flavor, a tobacco flavor, a toothpaste flavor, a chewing gum, a breath freshener, an orally dissolvable strips, a chewable candy, a hard candy, an oral care product, a tooth paste, a toothbrush, a dental floss, an oral rinse, an tooth whitener, a denture adhesive, a health care device, a tampon, a feminine napkin, an anti-inflammatory balm, an anti-inflammatory ointment, an anti-inflammatory spray, a disinfectant, a personal care product, a soap, a bar soap, a liquid soap, a bath fragrance, a body wash, a non-aerosol body spray, a body milk, a cleanser, a body cream, a hand sanitizer, a hand wash, a functional product base, a sunscreen lotion, a sunscreen spray, a deodorant, an anti-perspirant, an roll-on product, an aerosol product, a natural spray product, a wax-based deodorant, a glycol type deodorant, a soap type deodorant, a facial lotion, a body lotion, a hand lotion, a miscellaneous lotion, a body powder, a shave cream, a shave gel, a shave butter, a bath soak, a shower gel, an exfoliating scrub, a foot cream, a facial tissue, a cleansing wipe, a talc product, a hair care product, a hair care with ammonia, a shampoo, a hair conditioner, a hair rinse, a hair refresher, a hair fixative or styling aid, a hair bleach, a hair dye or colorant, a fabric care product, a fabric softener, a liquid fabric softener, a fabric softener sheet, a drier sheet, a fabric refresher, an ironing water, a detergent, a laundry detergent, a liquid laundry detergent, a powder laundry detergent, a tablet laundry detergent, a laundry detergent bar, a laundry detergent cream, a hand wash laundry detergent, a scent booster, a fragrance, a cologne, compounds, an encapsulated fragrance, a fine fragrance, a men's fine fragrance, a women's fine fragrance, a perfume, a solid perfume, an Eau De Toilette product, a natural spray product, a perfume spray product, an insect repellent product, and a wildlife scent.

Still within the scope of this invention is a method of imparting a cleanness and freshness sensation to a fabric product, the method comprising the step applying the microcapsule composition to the fabric product. The microcapsule composition can be incorporated in a fabric detergent, a fabric conditioner, or a dryer sheet for applying to the fabric product.

The details of one or more embodiments of the invention are set forth in the description below. Other features, objects, and advantages of the invention will be apparent from the description and the claims.

DETAILED DESCRIPTION OF THE INVENTION

Polyurea microcapsules of this invention each have a microcapsule core containing a fragrance or flavor and a microcapsule wall formed of polyurea as the encapsulating polymer. The microcapsule core has a high content of aldehydes. The encapsulating polymer is obtained through the interfacial polymerization between a polyisocyanate and a polyamine under certain conditions.

Conventional polyurea microcapsules face challenges in encapsulating a high content of aldehyde fragrance ingredients, especially aldehydes having low molecular weights such as decanal and octanal. In conventional polyurea microcapsules, aldehydes cannot be encapsulated at a high concentration (e.g., 1% or more). Viscosity buildup and increased particle size destabilize the microcapsules and render them useless.

This application is based on surprising discovery of certain processes that are particularly suitable for encapsulating aldehydes in polyurea microcapsules.

In one aspect of this invention, the polyurea microcapsule compositions are prepared by the steps of: (a) providing an oil-in-water emulsion containing (i) an aqueous phase as the continuous phase having a microcapsule formation aid, a polyamine, a water-soluble inorganic or organic salt of an alkali or alkaline earth metal, and water, and (ii) an oil phase as the dispersed phase having a fragrance and a polyisocyanate, (b) causing the formation of a microcapsule precursor having a microcapsule core and a microcapsule wall encapsulating the microcapsule core, in which the microcapsule core contains the fragrance, and the microcapsule wall is formed of the reaction product of the polyisocyanate and the polyamine, and (c) curing the microcapsule precursor to obtain the polyurea microcapsule composition as a microcapsule slurry, in which a plurality of polyurea microcapsules are dispersed in the aqueous phase.

In some embodiments, a fragrance emulsion is first prepared by mixing an aqueous solution and a fragrance oil phase at a high shearing rate in the range of 1000 revolutions per minute ("rpm") to 30000 rpm (e.g., 2000 rpm to 20000 rpm, 2000 rpm to 6000 rpm, 6000 rpm to 15000 rpm, 6500 rpm to 9500 rpm, 9000 rpm to 13500 rpm, 3000 rpm, 6500 rpm, 9500 rpm, 12500 rpm, and 13500 rpm). A plurality of oil droplets are formed and dispersed in the aqueous phase. The term "rpm" refers to revolution per minute as a measure of the frequency of rotation, which is the number of rotations around a fixed axis in one minute.

Preferably, one or more polyamines and one or more water-soluble inorganic or organic salts are then introduced to the fragrance emulsion to obtain the oil-in-water emulsion. The microcapsule wall is formed through the interfacial polymerization reaction between the polyisocyanate and the polyamine on the surface of the oil droplets. The one or more salts can be added before the addition of the polyamine or at the same time with polyamine. In some embodiments, the salts are added after the polyamine but before the formation of the encapsulating polymer. It is surprisingly found that adding the salts before the formation of encapsulating polymer leads to a stable microcapsule composition with a low viscosity and a high content of aldehydes (e.g., 2% or greater by weight of the composition). When the salts are added after the formation of the encapsulating polymer, viscosity is increased dramatically in the microcapsule composition having a high content of aldehydes.

Exemplary water-soluble inorganic or organic salts of an alkali or alkaline earth metal include sodium chloride, sodium sulfate, sodium carbonate, sodium bicarbonate, cesium carbonate, potassium chloride, potassium sulfate, potassium carbonate, potassium bicarbonate, lithium chloride, lithium sulfate, sodium ascorbate, sodium acetate, sodium benzoate, and the like. The salt can be added at an amount of 0.02% to 5% (e.g., 0.05% to 2% and 0.1% to 1%) by weight of the microcapsule composition. Preferably, the salt has a molecular weight of no more than 500 gram per mole (e.g., 30 g/mol to 400 g/mol and 35 g/mol to 300 g/mol).

The fragrance emulsion can also be formed by other known methods such as membrane filtration (see U.S. Pat.

Nos. 7,122,503 and 6,890,592) and microfluidics devices (see, US 2014/0045949, WO 2017/046299, WO 2017/137597, WO 2016/085742, WO 2016/085741, and WO 2016/085740).

The membrane filtration process uses (i) a membrane material having a pre-selected pore size, (ii) an oil phase containing a fragrance and polyisocyanate, and (iii) an aqueous phase containing a capsule formation aid, a water-soluble inorganic or organic salt of an alkali or alkaline earth metal, water, and optionally a polyamine. The oil phase is passed under pressure through the membrane into a moving or turbulent aqueous phase as the receiving solution, thereby forming an emulsion with uniform droplets of the oil phase dispersed in the aqueous phase. The microcapsule wall is then formed of an encapsulating polymer that is the reaction product between the polyisocyanate and the polyamine, in which the polyisocyanate is present in the oil phase, and the polyamine is either present in the aqueous phase or subsequently added to the emulsion.

The oil-in-water emulsion can also be prepared using a microfluidics device, wherein an aqueous phase and an oil phase are passed through individual channels and mixed in a microfluidics device as described in US 20140045949. The polyamine can be introduced to the aqueous phase before passing through the microfluidics device. Alternatively, a fragrance emulsion is first formed using an aqueous phase that is free of a polyamine. Subsequently, a polyamine is added to obtain the oil-in-water emulsion that has a plurality of oil droplets dispersed in an aqueous phase.

In any of the oil-in-water emulsions described above, the droplet sizes in diameter can vary in the range of 0.1 µm to 200 µm with a lower limit of 0.1 µm, 0.2 µm, 0.5 µm, 1 µm, 2 µm, 5 µm, 10 µm, 20 µm, or 30 µm and a upper limit of 200 µm, 150 µm, 120 µm, 100 µm, 90 µm, 80 µm, 60 µm, 50 µm, 40 µm, 30 µm, and 20 µm (e.g., 0.2 µm to 10 µm, 0.5 µm to 15 µm, 1 µm to 30 µm, 2 µm to 20 µm, and 15 µm to 40 µm). The weight ratio between the aqueous phase and the oil phase ranges from 10:1 to 1:2 (e.g., 5:1 to 1:1, 2:1 to 1:1, and 1.5:1).

The microcapsule compositions thus prepared contain a plurality of microcapsules dispersed in an aqueous phase. Each microcapsule has a microcapsule core and a microcapsule wall encapsulating the microcapsule core. The microcapsule core contains an active material (e.g., a fragrance, and a malodor counteractant). The microcapsule wall is formed of a polyurea polymer and has an inner surface and outer surface. The inner surface is in contact with the microcapsule core. The outer surface is in contact with the aqueous phase. Optionally, the outer surface is modified to attach one or more deposition groups to the outer surface each via a covalent bond. Each of the deposition groups, independently, contains a quaternary ammonium moiety, an oxoimidazolidinyl moiety, a catechol moiety, a carboxylic acid moiety, or an alkyl moiety.

The microcapsules in the compositions of this invention each have a particle size (in diameter) of 0.1 microns to 1000 microns (e.g., 0.5 microns to 500 microns, 1 micron to 200 microns, and 1 micron to 100 microns) with a lower limit of 0.1 microns, 0.5 microns, 1 micron, 2 microns, and 5 microns and an upper limit of 1000 microns, 500 microns, 200 microns, 100 microns, 75 microns, 50 microns, and 30 microns.

The microcapsules can be positively charged with a zeta potential of at least 10 mV (e.g., 25 mV or greater, 40 mV or greater, 25-200 mV, and 40-100 mV). Not to be bound by theory, the positively charged microcapsules have a strong affinity to specific animate and inanimate surfaces (e.g., hair and fabric), and also are unexpectedly stable in certain consumer product bases such as hair conditioners, shampoos, shower gels, and fabric conditioners.

The microcapsule has a core-shell structure with a single microcapsule core and a single microcapsule wall encapsulating the single microcapsule core. The microcapsule wall has an inner surface and outer surface. The inner surface is in contact with the microcapsule core. The outer surface is in contact with the environment where the microcapsule resides, e.g., a water phase, skin, and hair. The microcapsule contains 10 wt % to 99 wt % (e.g., 20 wt % to 95 wt %, 30 wt % to 95 wt %, and 40 wt % to 90 wt %) of the microcapsule core and 1 wt % to 90 wt % (e.g. 5 wt % to 80 wt %, 5 wt % to 70 wt %, and 10 wt % to 60 wt %) of the microcapsule wall.

The microcapsule core contains or consists of 20 wt % to 100 wt % (e.g., 30 wt % to 95 wt % and 40 wt % to 90 wt %) of an active material (e.g., a fragrance) and 0 wt % to 80 wt % (e.g., 5 wt % to 70 wt % and 10 wt % to 60 wt %) of a core solvent (such as caprylic/capric triglyceride). Preferably, the microcapsule core contains one or more aldehydes at a level of at least 2 wt % (e.g., at least 5 wt %, at least 6 wt %, 5 wt % to 95 wt %, and 6 wt % to 90 wt %). Preferably, each encapsulated aldehyde is not in an aldehyde precursor form. Further, it is not necessary to include an alkyl salicylate or a 2,2,2-trisubstituted acetal in the encapsulated fragrance. In the total encapsulated fragrance, the one or more aldehydes are preferably present at a level of at least 8% (e.g., at least 10%, 8% to 100%, 8% to 75%, and 10% to 90%) by weight of the total encapsulated fragrance.

The microcapsule wall is formed of an encapsulating polymer that is the reaction product of a polyfunctional nucleophile and a polyfunctional electrophile, preferably in the presence of a capsule formation aid (e.g., a dispersant or surfactant) and/or a catalyst (e.g., a base) so that an active material is encapsulated in the oil core by the microcapsule wall.

Preferably, the microcapsule has a microcapsule wall formed of an encapsulating polymer that is a reaction product of hexamethylene diamine or a branched polyethyleneimine (a polyfunctional nucleophile) and an aromatic or aliphatic polyisocyanate (a polyfunctional electrophile).

Polyfunctional Nucleophile.

The polyfunctional nucleophile can be a polyfunctional amine, a polyfunctional alcohol, or a mixture thereof. In a preferred embodiment, the polyfunctional nucleophile is a branched polyethyleneimine.

Suitable branched polyethyleneimines each have a molecular weight (e.g., weight average molecular weight, $M_w$) of 200 to 1,000,000 (e.g., 300 to 500,000, 500 to 200,000, 750 to 100,000, and 750 to 50,000). The average molecular weight range can be determined by light scattering as described in Barth H. G. and Mays J. W. Chemical Analysis Vol 113, "Modern Methods of Polymer Characterization."

The branched polyethyleneimines have a main chain and one or more side chains attached to the main chain. The main chain has 2 to 25,000 (e.g., 3 to 10,000, 5 to 5000, and 5 to 500) repeat ethylene amine (—$CH_2CH_2NH$—) units. The side chains each have one or more ethylene amine terminals (—$CH_2CH_2NH_2$). The representative structure of the branched polyethyleneimine is shown below:

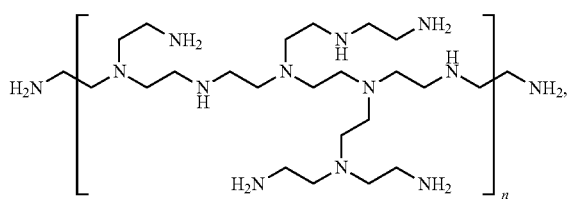

in which n is 1 to 5000 (e.g., 1 to 2000, 1 to 1000, and 1 to 100).

Other suitable polyfunctional amines ("polyamine") are those having at least a primary or secondary amine group (i.e., —NH₂ and —NH—) and one or more additional functional groups such as a primary or secondary amine and hydroxyl group (—OH). Exemplary polyfunctional amines include hexamethylenediamine, hexaethylenediamine, ethylenediamine, 1,3-diaminopropane, 1,2-diaminopropane, 1,4-diaminobutane, diethylenetriamine, pentaethylenehexamine, bis(3-aminopropyl)amine, bis(hexanethylene)triamine, tris(2-aminoethyl)amine, triethylenetetramine, N,N'-bis(3-aminopropyl)-1,3-propanediamine, N,N,N',N'-tetrakis (2-hydroxyethyl)ethylene diamine, N,N,N',N'-tetrakis(2-hydroxypropyl)ethylene diamine, 2,4-diamino-6-hydroxypyrimidine, 2,4,6-triaminopyrimidine, tetraethylenepentamine, amino-2-methyl-1-propanol, a second branched polyethylenimine, and chitosan. Guanidine amines and guanidine salts are yet another class of multifunctional amines of use in this invention. Exemplary guanidine amines and guanidine salts include, but are not limited to, 1,3-diaminoguanidine and its monohydrochloride, 1,1-dimethylbiguanide and its hydrochloride, guanidine carbonate, and guanidine hydrochloride. In a preferred embodiment, the polyfunctional amine is hexamethylenediamine, commercially available as DYTEK® HMD (by Invista, Wichita, KS), and 1,6-diaminohexane (Sigma-Aldrich, St. Louis, MO).

More suitable polyamines contain two or more amine groups such as —NH₂ and —R*NH, R* being substituted and unsubstituted $C_1$-$C_{20}$ alkyl, $C_1$-$C_{20}$ heteroalkyl, $C_1$-$C_{20}$ cycloalkyl, 3- to 8-membered heterocycloalkyl, aryl, and heteroaryl. These polyamines include polyalkylene polyamines and polyetheramines as described in WO 2015/023961 A1.

Amphoteric amines, i.e., amines that can react as an acid and a base, are another class of amines of use in this invention. Examples include proteins and amino acids such as L-lysine, D-lysine, L-arginine, D-arginine, L-lysine monohydrochloride, D-lysine monohydro-chloride, L-arginine monohydrochloride, D-arginine monohydrochloride, histidine, L-ornithine monohydrochloride, D-ornithine monohydrochloride, nisin, gelatin, and mixtures thereof.

Commercially available examples of polyamines include JEFFAMINE® EDR-148 (having a formula of NH₂—(CH₂CH₂O)ₓCH₂CH₂NH₂, where x=2), JEFFAMINE® EDR-176 (having a formula of NH₂—(CH₂CH₂O)ₓ CH₂CH₂NH₂, where x=3) (from Huntsman). Other polyether amines include the JEFFAMINE® ED Series, JEFFAMINE® TRIAMINES, polyethylenimines from BASF (Ludwigshafen, Germany) under LUPASOL® grades (e.g., Lupasol® FG, Lupasol® G20 waterfree, Lupasol® PR 8515, Lupasol® WF, Lupasol® FC, Lupasol® G20, Lupasol® G35, Lupasol® G100, Lupasol® G500, Lupasol® HF, Lupasol® PS, Lupasol® HEO 1, Lupasol® PN50, Lupasol® PN60, Lupasol® PO100 and Lupasol® SK). Other commercially available polyethylenimines include EPOMIN® P-1000, EPOMIN® P-1050, EPOMIN® RP18W and EPOMIN® PP-061 from NIPPON SHOKUBAI (New York, NY). Polyvinylamines such as those sold by BASF under LUPAMINE® grades can also be used. A wide range of polyetheramines may be selected by those skilled in the art.

Polyfunctional alcohols are those having two or more hydroxyl groups. Non-limiting examples are pentaerythritol, glucose, 2-aminoethanol, dipentaerythritol, glycerol, polyglycerol, ethylene glycol, hexylene glycol, polyethylene glycol, trimethylolpropane, neopentyl glycol, sorbitol, erythritol, threitol, arabitol, xylitol, ribitol, mannitol, galactitol, fucitol, iditol, inositol, volemitol, isomalt, maltitol, lactitol, maltotriitol, maltotetraitol, polyglycitol, and combinations thereof. More suitable polyfunctional alcohols are described in WO 2015/023961 A1.

The polyfunctional nucleophile as used in this invention can be a single compound (e.g., hexamethylene diamine and a branched polyethyleneimine) or a mixture of two or more polyfunctional amines (e.g., a branched polyethyleneimine with one or more polyfunctional amines/alcohols).

The range of polyfunctional nucleophile content can vary from 0.1% to 15% (e.g., 0.2% to 10%, 0.5% to 8%, 1% to 8%, and 2% to 6%) by weight of the microcapsule. In the microcapsule composition, the polyfunctional nucleophile is present at a level of 0.05% to 8% (e.g., 0.1% to 5%, 0.1% to 4%, 0.25% to 4%, and 0.25% to 3%) by weight of the microcapsule composition.

In one embodiment, the polyfunctional nucleophile is added to the polymerization reaction at a temperature of 0-55° C. (e.g., 10-50° C., 15-45° C., 20-40° C., 30-40° C. and 25-35° C.).

Polyfunctional Electrophiles

The polyfunctional electrophile has at least two electrophilic functional groups reactive towards the branched polyethyleneimine, the polyfunctional amine, or the polyfunctional alcohol to form a network of the encapsulating polymer. Examples of the electrophilic group include formyl, keto, carboxyl, an isocyanate group, a carboxylate ester group, an acyl halide group, an amide group, a carboxylic anhydride group, an alkyl halide group, an epoxide group, an aziridine group, an oxetane group, an azetidine group, a sulfonyl halide group, a chlorophosphate group, an α,β-unsaturated carbonyl group, an α,β-unsaturated nitrile group, a trifluoromethane-sulfonate group, a p-toluene-sulfonate group, and an α,β-unsaturated methanesulfonyl group.

Suitable polyfunctional electrophiles include glutaric dialdehyde and succinic dialdehyde; as well as compounds such as glyoxyl trimer and paraformaldehyde, bis(dimethyl) acetal, bis(diethyl) acetal, polymeric dialdehydes, such as oxidized starch. Other suitable polyfunctional electrophiles are a low molecular weight, difunctional aldehyde, such as glyoxal, 1,3-propane dialdehyde, 1,4-butane dialdehyde, 1,5-pentane dialdehyde, or 1,6-hexane dialdehyde.

Other suitable polyfunctional electrophiles are polyfunctional isocyanates (i.e., polyisocyanates), each of which contains two or more isocyanate (—NCO) groups. These polyisocyanates can be aromatic, aliphatic, linear, branched, or cyclic. In some embodiments, the polyisocyanate contains, on average, 2 to 4 isocyanate groups. In particular embodiments, the polyisocyanate contains at least three isocyanate functional groups. In certain embodiments, the polyisocyanate is water insoluble.

In particular embodiments, the polyisocyanate used in this invention is an aromatic polyisocyanate. Desirably, the aromatic polyisocyanate includes a phenyl, tolyl, xylyl, naphthyl or diphenyl moiety as the aromatic component. In certain embodiments, the aromatic polyisocyanate is a polyisocyanurate of toluene diisocyanate, a trimethylol propane-adduct of toluene diisocyanate or a trimethylol propane-adduct of xylylene diisocyanate.

One class of suitable aromatic polyisocyanates are those having the generic structure shown below, and its structural isomers

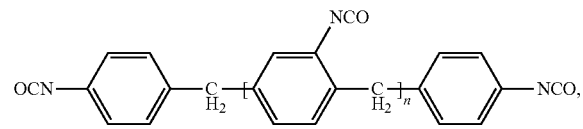

wherein n can vary from zero to a desired number (e.g., 0-50, 0-20, 0-10, and 0-6) depending on the type of polyamine or polyol used. Preferably, the number of n is limited to less than 6. The starting polyisocyanate may also be a mixture of polyisocyanates where the value of n can vary from 0 to 6. In the case where the starting polyisocyanate is a mixture of various polyisocyanates, the average value of n preferably falls in between 0.5 and 1.5. Commercially-available polyisocyanates include LUPRANATE® M20 (chemical name: polymeric methylene diphenyl diisocyanate, i.e., "PMDI"; commercially available from BASF containing isocyanate group "NCO" 31.5 wt %), where the average n is 0.7; PAPI® 27 (PMDI commercially available from Dow Chemical having an average molecular weight of 340 and containing NCO 31.4 wt %) where the average n is 0.7; MONDUR® MR (PMDI containing NCO at 31 wt % or greater, commercially available from Covestro, Pittsburgh, Pennsylvania) where the average n is 0.8; MONDUR® MR Light (PMDI containing NCO 31.8 wt %, commercially available from Covestro) where the average n is 0.8; MONDUR® 489 (PMDI commercially available from Covestro containing NCO 30-31.4 wt %) where the average n is 1; poly[(phenylisocyanate)-co-formaldehyde] (Aldrich Chemical, Milwaukee, WI), other isocyanate monomers such as DESMODUR® N3200 (poly(hexamethylene diisocyanate) commercially available from Covestro), and Takenate® D-110N (trimethylol propane-adduct of xylylene diisocyanate, Mitsui Chemicals America, Inc., Rye Brook, NY, containing NCO 11.5 wt %), DESMODUR® L75 (a polyisocyanate base on toluene diisocyanate commercially available from Covestro), and DESMODUR® IL (another polyisocyanate based on toluene diisocyanate commercially available from Covestro).

The structures of certain commercially available polyisocyanates of the invention are shown below:

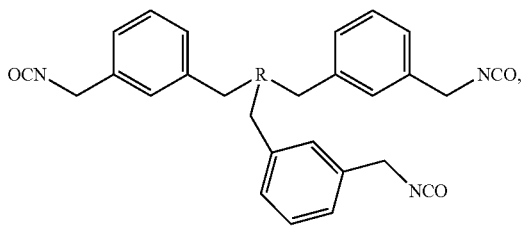

or its structural isomer. R can be a $C_1$-$C_{10}$ alkyl, $C_1$-$C_{10}$ ester, or an isocyanurate. Representative polyisocyanates of this structure are TAKENATE® D-110N (Mitsui), DESMODUR® L75 (Covestro), and DESMODUR® IL (Covestro).

Polyisocyanate Takenate® D-110N and other polyisocyanates are commercially available, typically in an ethyl acetate solution. Preferably, ethyl acetate is replaced with a solvent having a high flash point (e.g., at least 100° C., at least 120° C., and at least 150° C.). Suitable solvents include triacetin, triethyl citrate, ethylene glycol diacetate, benzyl benzoate, and combinations thereof.

As an illustration, Takenate® D-110N (a trimethylol propane-adduct of xylylene diisocyanate solution in ethyl acetate) is combined with benzyl benzoate and vacuum distilled to remove ethyl acetate to obtain a polyisocyanate solution containing 59% of the trimethylol propane-adduct of xylylene diisocyanate solution and 41% of benzyl benzoate. This polyisocyanate solution has a flash point of at least 60° C. This polyisocyanate solution in benzyl benzoate is suitable for preparing the microcapsule composition of this invention.

Other examples of the aromatic polyisocyanate include 1,5-naphthylene diisocyanate, 4,4'-diphenylmethane diisocyanate (MDI), hydrogenated MDI (H12MDI), xylylene diisocyanate (XDI), tetramethylxylol diisocyanate (TMXDI), 4,4'-diphenyldimethylmethane diisocyanate, di- and tetraalkyldiphenylmethane diisocyanate, 4,4'-dibenzyl diisocyanate, 1,3-phenylene diisocyanate, 1,4-phenylene diisocyanate, the isomers of tolylene diisocyanate (TDI), 4,4'-diisocyanatophenyl perfluoroethane, phthalic acid bisisocyanatoethyl ester, also polyisocyanates with reactive halogen atoms, such as 1-chloromethylphenyl 2,4-diisocyanate, 1-bromomethyl-phenyl 2,6-diisocyanate, and 3,3-bis-chloromethyl ether 4,4'-diphenyldiisocyanate, and combinations thereof.

In other particular embodiments, the polyisocyanate is an aliphatic polyisocyanate such as a trimer of hexamethylene diisocyanate, a trimer of isophorone diisocyanate, and a biuret of hexamethylene diisocyanate. Exemplary aliphatic polyisocyanates include those commercially available, e.g., BAYHYDUR® N304 and BAYHYDUR® N305, which are aliphatic water-dispersible polyisocyanates based on hexamethylene diisocyanate; DESMODUR® N3600, DESMODUR® N3700, and DESMODUR® N3900, which are low viscosity, polyfunctional aliphatic polyisocyanates based on hexamethylene diisocyanate; and DESMODUR® 3600 and DESMODUR® N100 which are aliphatic polyisocyanates based on hexamethylene diisocyanate, each of which is available from Covestro, Pittsburgh, PA). More examples include 1-methyl-2,4-diisocyanatocyclohexane, 1,6-diisocyanato-2,2,4-trimethylhexane, 1,6-diisocyanato-2,4,4-trimethylhexane, 1-isocyanatomethyl-3-isocyanato-1,5,5-trimethylcyclohexane, chlorinated and brominated diisocyanates, phosphorus-containing diisocyanates, tetramethoxybutane 1,4-diisocyanate, butane 1,4-diisocyanate, hexane 1,6-diisocyanate (HDI), dicyclohexylmethane diisocyanate, cyclohexane 1,4-diisocyanate, ethylene diisocyanate, and combinations thereof. Sulfur-containing polyisocyanates are obtained, for example, by reacting hexamethylene diisocyanate with thiodiglycol or dihydroxydihexyl sulfide. Further suitable diisocyanates are trimethylhexamethylene diisocyanate, 1,4-diisocyanatobutane, 1,2-diisocyanatododecane, dimer fatty acid diisocyanate, and combinations thereof.

The weight average molecular weight of certain polyisocyanates useful in this invention varies from 250 Da to 1000 Da and preferable from 275 Da to 500 Da.

The range of the polyfunctional electrophile (e.g., the polyisocyanate) content can vary from 0.2% to 40% (e.g., 0.4% to 35%, 0.5% to 30%, 1% to 25%, 2% to 25%, and 5% to 20%) by weight of the microcapsule. When the microcapsule is incorporated in a microcapsule composition, the amount of the polyisocyanate varies from 0.1% to 20%, preferably from 0.1% to 15%, more preferably from 0.2% to 10%, and even more preferably from 1.5% to 3.5%, all based on the total capsule composition.

In some embodiments, the polyfunctional isocyanate used in the preparation of the microcapsules of this invention is a single polyisocyanate. In other embodiments the polyisocyanate is a mixture of two or more polyisocyanates. In some embodiments, the mixture of polyisocyanates includes an aliphatic polyisocyanate and an aromatic polyisocyanate. In particular embodiments, the mixture of polyisocyanates is a biuret of hexamethylene diisocyanate and a trimethylol propane-adduct of xylylene diisocyanate. In certain embodiments, the polyisocyanate is an aliphatic isocyanate or a mixture of aliphatic isocyanate, free of any aromatic isocyanate. In other words, in these embodiments, no aromatic isocyanate is used to prepare the polyurea/polyurethane polymers as capsule wall materials. More examples of suitable polyisocyanates can be found in WO 2004/054362 and WO 2017/192648.

Capsule Formation Aids

The microcapsule composition is typically prepared in the presence of a capsule formation aid, which can be a surfactant or dispersant. Capsule formation aids stabilize microcapsules suspended in an aqueous phase and also improve the performance of the microcapsule composition. Performance is typically measured by the intensity of the fragrance released during certain stages, e.g., the pre-rub and post-rub phases in laundry applications. The pre-rub phase is the phase when the capsules have been deposited on the cloth, e.g., after a wash cycle using a capsule-containing fabric softener or detergent. The post-rub phase is the phase after the capsules have been deposited and are broken by friction or other similar mechanisms.

In some embodiments, the capsule formation aid is a protective colloid or emulsifier including, e.g., maleic-vinyl copolymers such as the copolymers of vinyl ethers with maleic anhydride or acid, sodium lignosulfonates, maleic anhydride/styrene copolymers, ethylene/maleic anhydride copolymers, and copolymers of propylene oxide and ethylene oxide, polyvinylpyrrolidone (PVP), polyvinyl alcohols (PVA), sodium salt of naphthalene sulfonate condensate, carboxymethyl cellulose (CMC), fatty acid esters of poly-oxyethylenated sorbitol, sodium dodecylsulfate, and combinations thereof. The concentration of the capsule formation aid (e.g., the surfactant and dispersant) varies from 0.1% to 5% (e.g., 0.2% to 4%, 0.5% to 4%, 0.5% to 2.5%, and 1% to 2%) by weight of the microcapsule composition.

Suitable capsule formation aids include commercially available surfactants such as sulfonated naphthalene-formaldehyde condensates under the trade name MORWET® D-425 (sodium salt of alkylnaphthalenesulfonate formaldehyde condensate, Akzo Nobel, Fort Worth, Texas); partially hydrolyzed polyvinyl alcohols under the name MOWIOL®, e.g., MOWIOL® 3-83 (Kuraray, Houston, Texas); ethylene oxide-propylene oxide block copolymers or poloxamers under the trade names PLURONIC®, SYNPERONIC® or PLURACARE® materials (BASF); sulfonated polystyrenes under the trade name FLEXAN® II (Akzo Nobel); ethylene-maleic anhydride polymers under the trade name ZEMAC® (Vertellus Specialties Inc., Indianapolis, Indiana); and Poly-quaternium series such as Polyquaternium-11 ("PQ-11" a copolymer of vinyl pyrrolidone and quaternized dimethyl-aminoethyl methacrylate; sold by BASF as LUVIQUAT® PQ11 AT 1).

Processing aids can also be used as capsule formation aids. They include hydrocolloids, which improve the colloidal stability of the slurry against coagulation, sedimentation and creaming. The term "hydrocolloid" refers to a broad class of water-soluble or water-dispersible polymers having anionic, cationic, zwitterionic or non-ionic character. Hydrocolloids useful in the present invention include, but are not limited to, polycarbohydrates, such as starch, modified starch, dextrin, maltodextrin, and cellulose derivatives, and their quaternized forms; natural gums such as alginate esters, carrageenan, xanthanes, agar-agar, pectines, pectic acid, and natural gums such as gum arabic, gum tragacanth and gum karaya, guar gums and quaternized guar gums; gelatine, protein hydrolysates and their quaternized forms; synthetic polymers and copolymers, such as poly(vinyl pyrrolidone-co-vinyl acetate), poly(vinyl alcohol-co-vinyl acetate), poly((met)acrylic acid), poly(maleic acid), poly(alkyl(meth)acrylate-co-(meth)acrylic acid), poly(acrylic acid-co-maleic acid)copolymer, poly(alkyleneoxide), poly(vinyl-methylether), poly(vinylether-co-maleic anhydride), and the like, as well as poly-(ethyleneimine), poly((meth)acrylamide), poly(alkyleneoxide-co-dimethylsiloxane), poly(amino dimethylsiloxane), and the like, and their quaternized forms. The capsule formation aid may also be used alone or in combination with carboxymethyl cellulose ("CMC"), polyvinylpyrrolidone, polyvinyl alcohol, and alkylnaphthalenesulfonate formaldehyde condensates during processing to facilitate capsule formation. Examples of these surfactants include cetyl trimethyl ammonium chloride (CTAC), poloxamers such as PLURONICS® (e.g., PLURONIC® F127), PLURAFAC® (e.g., PLURAFAC® F127), or MIRANET-N®, saponins such as QNATURALE® (National Starch Food Innovation); or a gum Arabic such as Seyal or Senegal. In certain embodiments, the CMC polymer has a molecular weight (e.g., weight average molecular weight) range between 90,000 Daltons to 1,500,000 Daltons, preferably between 250,000 Daltons to 750,000 Daltons and more preferably between 400,000 Daltons to 750,000 Daltons. The CMC polymer has a degree of substitution between 0.1 to 3, preferably between 0.65 to 1.4, and more preferably between 0.8 to 1. The CMC polymer is optionally present in the capsule composition at a level from 0.1% to 2% and preferably from 0.3% to 0.7%. In other embodiments, polyvinylpyrrolidone used in this invention is a water-soluble polymer and has a molecular weight (e.g., weight average molecular weight) of 1,000 Daltons to 10,000,000 Daltons. Suitable polyvinylpyrrolidones are polyvinylpyrrolidones K12, K15, K17, K25, K30, K60, K90, or a mixture thereof. The amount of the polyvinylpyrrolidone is 0.1% to 50% with a lower limit of 0.1%, 0.2%, 0.5%, 1%, 1.5%, 2%, 3%, 5% or 7% and an upper limit of 50%, 40%, 30%, 25%, 20%, 15%, 10%, 8%, 6%, 5%, 4%, 3%, 2%, or 1% (e.g., 5% to 30%, and 10% to 25%) by weight of the microcapsule composition.

Catalysts

Catalysts ae sometimes added to the oil-in-water emulsion to facilitate the polymerization reaction. Catalysts suitable for use in the invention are metal carbonates, metal hydroxide, amino or organometallic compounds and include, for example, sodium carbonate, cesium carbonate, potassium carbonate, lithium hydroxide, 1,4-diazabicyclo[2.2.2]octane (i.e., DABCO), N,N-dimethylaminoethanol, N,N-dimethyl-cyclohexylamine, bis-(2-dimethylaminoethyl) ether, N,N dimethylacetylamine, stannous octoate, and dibutyltin dilaurate.

Other Encapsulating Polymers and Microcapsules

The encapsulating polymer can be a hybrid polymer, which contains a first polymer and a second polymer. See WO 2017/058875. In one embodiment, the first polymer is a sol-gel polymer (e.g., silica gel and polyalkylsiloxane), and the second polymer is polyacrylate, polyacrylamide, poly(acrylate-co-acrylamide), polyurea, polyurethane, starch, gelatin and gum Arabic, poly(melamine-formaldehyde), poly(urea-formaldehyde), or a combination thereof. A preferred embodiment is a hybrid capsule having silica gel as the first polymer, and polyurea as the second polymer.

Further, the microcapsule composition of this invention optionally has a second, third, fourth, fifth, or sixth microcapsule each formed of an encapsulating polymer selected from the group consisting of a sol-gel polymer (e.g., silica), polyacrylate, polyacrylamide, poly(acrylate-co-acrylamide), polyurea, polyurethane, starch, gelatin and gum Arabic, poly(melamine-formaldehyde), poly(urea-formaldehyde), and combinations thereof. A branched polyethyleneimine and its derivatives can also be coated onto the microcapsule wall to prepare a microcapsule having a positive zeta potential.

These encapsulating polymers are described in detail below.

Sol-gel Microcapsules. These microcapsules have a microcapsule wall formed of a sol-gel polymer, which is a reaction product of a sol-gel precursor via a polymerization reaction (e.g., hydrolyzation). Suitable sol-gel precursors are compounds capable of forming gels such as compounds containing silicon, boron, aluminum, titanium, zinc, zirconium, and vanadium. Preferred precursors are organosilicon, organoboron, and organoaluminum including metal alkoxides and b-diketonates.

Sol-gel precursors suitable for the purposes of the invention are selected in particular from the group of di-, tri- and/or tetrafunctional silicic acid, boric acid and alumoesters, more particularly alkoxysilanes (alkyl orthosilicates), and precursors thereof.

One example of sol-gel precursors suitable for the purposes of the invention are alkoxysilanes corresponding to the following general formula:

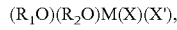

$(R_1O)(R_2O)M(X)(X')$, wherein X can be hydrogen or —$OR_3$; X' can be hydrogen or —$OR_4$; and $R_1$, $R_2$, $R_3$ and $R_4$ independently represent an organic group, more particularly a linear or branched alkyl group, preferably a $C_1$-$C_{12}$ alkyl. M can be Si, Ti, or Zr.

A preferred sol/gel precursor is alkoxysilanes corresponding to the following general formula: $(R_1O)(R_2O)Si(X)(X')$, wherein each of X, X', $R_1$, and $R_2$ are defined above.

Particularly preferred compounds are the silicic acid esters such as tetramethyl orthosilicate (TMOS) and tetraethyl orthosilicate (TEOS). A preferred compound includes Dynasylan® (organofunctional silanes commercially available from Degussa Corporation, Parsippany New Jersey, USA). Other sol-gel precursors suitable for the purposes of the invention are described, for example, in German Patent Application DE10021165. These sol-gel precursors are various hydrolyzable organosilanes such as, for example, alkylsilanes, alkoxysilanes, alkyl alkoxysilanes and organoalkoxysilanes. Besides the alkyl and alkoxy groups, other organic groups (for example allyl groups, aminoalkyl groups, hydroxyalkyl groups, etc.) may be attached as substituents to the silicon.

Recognizing that metal and semi metal alkoxide monomers (and their partially hydrolyzed and condensed polymers) such as tetramethoxy silane (TMOS), tetraethoxy silane (TEOS), etc. are very good solvents for numerous molecules and active ingredients is highly advantageous since it facilitates dissolving the active materials at a high concentration and thus a high loading in the final capsules.

Polyacrylate microcapsules, polyacrylamide microcapsules, and poly(acrylate-co-acrylamide) microcapsules. These microcapsules are prepared from corresponding precursors, which form the microcapsule wall. Preferred precursor are bi- or polyfunctional vinyl monomers including by way of illustration and not limitation, allyl methacrylate/acrylamide, triethylene glycol dimethacrylate/acrylamide, ethylene glycol dimethacrylate/acrylamide, diethylene glycol dimethacrylate/acrylamide, triethylene glycol dimethacrylate/acrylamide, tetraethylene glycol dimethacrylate/acrylamide, propylene glycol dimethacrylate/acrylamide, glycerol dimethacrylate/acrylamide, neopentyl glycol dimethacrylate/acrylamide, 1,10-decanediol dimethacrylate/acrylamide, pentaerythritol trimethacrylate/acrylamide, pentaerythritol tetramethacrylate/acrylamide, dipentaerythritol hexamethacrylate/acrylamide, triallyl-formal trimethacrylate/acrylamide, trimethylol propane trimethacrylate/acrylamide, tributanediol dimethacrylate/acrylamide, aliphatic or aromatic urethane diacrylates/acrylamides, difunctional urethane acrylates/acrylamides, ethoxylated aliphatic difunctional urethane methacrylates/acrylamides, aliphatic or aromatic urethane dimethacrylates/acrylamides, epoxy acrylates/acrylamides, epoxymethacrylates/acrylamides, 1,3-butylene glycol diacrylate/acrylamide, 1,4-butanediol dimethacrylate/acrylamide, 1,4-butaneidiol diacrylate/acrylamide, diethylene glycol diacrylate/acrylamide, 1,6-hexanediol diacrylate/acrylamide, 1,6-hexanediol dimethacrylate/acrylamide, neopentyl glycol diacrylate/acrylamide, polyethylene glycol diacrylate/acrylamide, tetraethylene glycol diacrylate/acrylamide, triethylene glycol diacrylate/acrylamide, 1,3-butylene glycol dimethacrylate/acrylamide, tripropylene glycol diacrylate/acrylamide, ethoxylated bisphenol diacrylate/acrylamide, ethoxylated bisphenol dimethylacrylate/acrylamide, dipropylene glycol diacrylate/acrylamide, alkoxylated hexanediol diacrylate/acrylamide, alkoxylated cyclohexane dimethanol diacrylate/acrylamide, propoxylated neopentyl glycol diacrylate/acrylamide, trimethylolpropane triacrylate/acrylamide, pentaerythritol triacrylate/acrylamide, ethoxylated trimethylolpropane triacrylate/acrylamide, propoxylated trimethylolpropane triacrylate/acrylamide, propoxylated glyceryl triacrylate/acrylamide, ditrimethyloipropane tetraacrylate/acrylamide, dipentaerythritol pentaacrylate/acrylamide, ethoxylated pentaerythritol tetraacrylate/acrylamide, PEG 200 dimethacrylate/acrylamide, PEG 400 dimethacrylate/acrylamide, PEG 600 dimethacrylate/acrylamide, 3-acryloyloxy glycol monoacrylate/acrylamide, triacryl formal, triallyl isocyanate, and triallyl isocyanurate.

The monomer is typically polymerized in the presence of an activation agent (e.g., an initiator) at a raised temperature (e.g., 30-90° C.) or under UV light. Exemplary initiators are 2,2'-azobis(isobutyronitrile) ("AIBN"), dicetyl peroxydicarbonate, di(4-tert-butylcyclohexyl) peroxydicarbonate, dioctanoyl peroxide, dibenzoyl peroxide, dilauroyl peroxide, didecanoyl peroxide, tert-butyl peracetate, tert-butyl perlaurate, tert-butyl perbenzoate, tert-butyl hydroperoxide, cumene hydroperoxide, cumene ethylperoxide, diisopropylhydroxy dicarboxylate, 2,2'-azobis(2,4-dimethylvaleronitrile), 1,1'-azobis-(cyclohexane-1-carbonitrile), dimethyl 2,2'-azobis(2-methylpropionate), 2,2'-azobis[2-methyl-N-(2-hydroxyethyl) propionamide, sodium persulfate, benzoyl peroxide, and combinations thereof.

Emulsifiers used in the formation of polyacrylate/polyacrylamide/poly(acrylate-co-acrylamide) capsule walls are typically anionic emulsifiers including by way of illustration and not limitation, water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesulfonate, sodium dialkylsulfosuccinates, dioctyl sulfosuccinate, sodium dilaurylsulfosuccinate, poly(styrene sulfonate) sodium salt, isobutylene-maleic anhydride copolymer, gum arabic, sodium alginate, carboxymethylcellulose, cellulose sulfate and pectin, poly(styrene sulfonate), isobutylene-maleic anhydride copolymer, gum arabic, carrageenan, sodium alginate, pectic acid, tragacanth gum, almond gum and agar; semi-synthetic polymers such as carboxymethyl cellulose, sulfated cellulose, sulfated methylcellulose, carboxymethyl starch, phosphated starch, lignin sulfonic acid; and synthetic polymers such as maleic anhydride copolymers (including hydrolyzates thereof), polyacrylic acid, polymethacrylic acid, acrylic acid butyl acrylate copolymer or crotonic acid homopolymers and copolymers, vinylbenzenesulfonic acid or 2-acrylamido-2-methylpropanesulfonic acid homopolymers and copolymers, and partial amide or partial ester of such polymers and copolymers, carboxymodified polyvinyl alcohol, sulfonic acid-modified polyvinyl alcohol and phosphoric acid-modified polyvinyl alcohol, phosphated or sulfated tristyrylphenol ethoxylates. The amount of anionic emulsifier is anywhere from 0.1 to 40 percent by weight of all constituents, more preferably from 0.5 to 10 percent, more preferably 0.5 to 5 percent by weigh.

Aminoplasts and Gelatin. A representative process used for aminoplast encapsulation is disclosed in U.S. Pat. No. 3,516,941 and US 2007/0078071, though it is recognized that many variations with regard to materials and process steps are possible. Another encapsulation process, i.e., gelatin encapsulation, is disclosed in U.S. Pat. No. 2,800,457. Both processes are discussed in the context of fragrance encapsulation for use in consumer products in U.S. Pat. Nos. 4,145,184 and 5,112,688 respectively. Polymer systems are well-known in the art and non-limiting examples of these include aminoplast capsules and encapsulated particles as disclosed in GB 2006709 A; the production of microcapsules having walls comprising styrene-maleic anhydride reacted with melamine-formaldehyde precondensates as disclosed in U.S. Pat. No. 4,396,670; an acrylic acid-acrylamide copolymer, cross-linked with a melamine-formaldehyde resin as disclosed in U.S. Pat. No. 5,089,339; capsules composed of cationic melamine-formaldehyde condensates as disclosed in U.S. Pat. No. 5,401,577; melamine formaldehyde microencapsulation as disclosed in U.S. Pat. No. 3,074,845; amido-aldehyde resin in-situ polymerized capsules disclosed in EP 0 158 449 A1; etherified urea-formaldehyde polymer as disclosed in U.S. Pat. No. 5,204,185; melamine-formaldehyde microcapsules as described in U.S. Pat. No. 4,525,520; cross-linked oil-soluble melamine-formaldehyde precondensate as described in U.S. Pat. No. 5,011,634; capsule wall material formed from a complex of cationic and anionic melamine-formaldehyde precondensates that are then cross-linked as disclosed in U.S. Pat. No. 5,013,473; polymeric shells made from addition polymers such as condensation polymers, phenolic aldehydes, urea aldehydes or acrylic polymer as disclosed in U.S. Pat. No. 3,516,941; urea-formaldehyde capsules as disclosed in EP 0 443 428 A2; melamine-formaldehyde chemistry as disclosed in GB 2 062 570 A; and capsules composed of polymer or copolymer of styrene sulfonic acid in acid of salt form, and capsules cross-linked with melamine-formaldehyde as disclosed in U.S. Pat. No. 4,001,140.

Urea-formaldehyde and melamine-formaldehyde Capsules. Urea-formaldehyde and melamine-formaldehyde pre-condensate capsule shell wall precursors are prepared by means of reacting urea or melamine with formaldehyde where the mole ratio of melamine or urea to formaldehyde is in the range of from 10:1 to 1:6, preferably from 1:2 to 1:5. For purposes of practicing this invention, the resulting material has a molecular weight in the range of from 156 to 3000. The resulting material may be used 'as-is' as a cross-linking agent for the aforementioned substituted or un-substituted acrylic acid polymer or copolymer or it may be further reacted with a $C_1$-$C_6$ alkanol, e.g., methanol, ethanol, 2-propanol, 3-propanol, 1-butanol, 1-pentanol or 1-hexanol, thereby forming a partial ether where the mole ratio of melamine/urea:formaldehyde:alkanol is in the range of 1:(0.1-6):(0.1-6). The resulting ether moiety-containing product may be used 'as-is' as a cross-linking agent for the aforementioned substituted or un-substituted acrylic acid polymer or copolymer, or it may be self-condensed to form dimers, trimers and/or tetramers which may also be used as cross-linking agents for the aforementioned substituted or un-substituted acrylic acid polymers or co-polymers. Methods for formation of such melamine-formaldehyde and urea-formaldehyde pre-condensates are set forth in U.S. Pat. No. 6,261,483, and Lee et al. (2002) *J. Microencapsulation* 19, 559-569.

Examples of urea-formaldehyde pre-condensates useful in the practice of this invention are URAC® 180 and URAC® 186, trademarks of Cytec Technology Corp. of Wilmington, DE. Examples of melamine-formaldehyde pre-condensates useful in the practice if this invention, include, but are not limited to, CYMEL® U-60, CYMEL® U-64 and CYMEL® U-65, trademarks of Cytec Technology Corp. of Wilmington, DE. It is preferable to use, as the precondensate for cross-linking, the substituted or un-substituted acrylic acid polymer or co-polymer. In practicing this invention, the range of mole ratios of urea-formaldehyde precondensate/melamine-formaldehyde pre-condensate to substituted/un-substituted acrylic acid polymer/co-polymer is in the range of from 9:1 to 1:9, preferably from 5:1 to 1:5 and most preferably from 2:1 to 1:2.

In one embodiment of the invention, microcapsules with polymer(s) composed of primary and/or secondary amine reactive groups or mixtures thereof and cross-linkers can also be used. See US 2006/0248665. The amine polymers can possess primary and/or secondary amine functionalities and can be of either natural or synthetic origin. Amine-containing polymers of natural origin are typically proteins such as gelatin and albumen, as well as some polysaccharides. Synthetic amine polymers include various degrees of hydrolyzed polyvinyl formamides, polyvinylamines, polyallyl amines and other synthetic polymers with primary and secondary amine pendants. Examples of suitable amine polymers are the LUPAMIN® series of polyvinyl formamides available from BASF. The molecular weights of these materials can range from 10,000 to 1,000,000.

Urea-formaldehyde or melamine-formaldehyde capsules can also include formaldehyde scavengers, which are capable of binding free formaldehyde. When the capsules are for use in aqueous media, formaldehyde scavengers such as sodium sulfite, melamine, glycine, and carbohydrazine are suitable. When the capsules are aimed to be used in products having low pH, e.g., fabric care conditioners, formaldehyde scavengers are preferably selected from beta diketones, such as beta-ketoesters, or from 1,3-diols, such as propylene glycol. Preferred beta-ketoesters include alkylmalonates, alkyl aceto acetates and polyvinyl alcohol aceto acetates.

The microcapsule composition of this invention optionally contains one or more additional microcapsules, e.g., a second, third, fourth, fifth, or sixth microcapsules. Each of these microcapsules can be any of the microcapsule described above.

These additional microcapsules can be any of the microcapsules described above but different from each other in term of the microcapsule size, the degree of polymerization, the degree of crosslinking, the encapsulating polymer, the thickness of the wall, the active material, the ratio between the wall material and the active material, the rupture force or fracture strength, and the like.

Active Materials

The microcapsule compositions of the invention are especially suitable to encapsulate in the capsule core a fragrance containing 8 wt % to 100 wt % one or more aldehydes by weight of the fragrance. In some embodiments, each of one or more aldehydes has a C log P of 4 or lower. In other embodiments, each of the one or more aldehydes has a molecular weight of 200 Daltons or lower. Among the one or more aldehydes, some do not have a substitution on the alpha and/or beta carbon position relative to any aldehyde function group (—CHO) on the aldehyde (aldehyde A), and some have a substitution on the alpha or beta carbon position and have a C log P value of 4 and below (aldehyde B). None of the aldehydes has a hemiacetal structure, namely, not an aldehyde precursor. Optionally, the fragrance contains 2 wt % to 100 wt % of aldehydes with a substitution on the alpha or beta carbon position and having a C log P of 4 or greater. In some embodiments, the wt % of aldehydes in the fragrance excludes the weight of lilial (C log P 4.11) and hexyl cinnamic aldehyde (HCA, C log P 4.86). Both Lilial and HCA have a high C log P, indicating low hydrophilicity. Aldehydes with a C log P higher than 4 can be successfully encapsulated in a conventional polyurea microcapsule due to their low hydrophilicity and low reactivity toward polyamine in the aqueous phase during the preparation of the microcapsule.

The C log P of many perfume ingredients has been reported, for example, the Ponoma92 database, available from Daylight Chemical Information Systems, Inc. (Daylight CIS) Irvine, California. The values are most conveniently calculated using C log P program also available from Daylight CIS. The program also lists experimentally determined log P values when available from the Pomona database. The calculated log P (C log P) is normally determined by the fragment approach on Hansch and Leo (A. Leo, in Comprehensive Medicinal Chemistry, Vol. 4, C. Hansch, P. G. Sammens, J. B. Taylor and C. A. Ransden, Editiors, p. 295 Pergamon Press, 1990). This approach is based upon the chemical structure of the fragrance ingredient and takes into account the numbers and types of atoms, the atom connectivity and chemical bonding. The C log P values which are most reliable and widely used estimates for this physiochemical property can be used instead of the experimental Log P values useful in the present invention. Further information regarding C log P and log P values can be found in U.S. Pat. No. 5,500,138. In this application, C log P and log P are used interchangeably.

It is known that aldehydes react with the polyamine used in the encapsulation process, which leads to poor capsule formation and aggregation. See WO2011/161265 A2. The extent or severity of aggregation depends on a number of factors including the reactivity of the aldehyde towards the polyamine employed in the capsule-forming process as well as the solubility of the aldehyde in aqueous media and its C log P, the extent to which an aldehyde will partition into the aqueous phase from the oil phase. See id., page 5. Linear aldehydes, i.e. those aldehydes having no substituents at the positions alpha or beta to the aldehyde carbonyl group are relatively reactive and if they are not effectively protected in their precursor form they are likely to cause significant agglomeration problems. See id. To avoid the agglomeration problems, WO 2011/161265 describes a method of converting the aldehydes to a protected form before encapsulating them in a microcapsule.

One aspect of this invention relates to the surprising discovery a process to encapsulating aldehydes in polyurea microcapsules without converting them to their protected form. This process is in particular suitable for encapsulating aldehydes having a low C log P (e.g., 4 or less, 3.5 or less, 3 or less, 1 to 4, and 2 to 4), a low molecular weight (e.g., 200 or less, 190 or less, 60 to 200, and 100 to 200), a high water solubility (e.g., 1 mg/L or greater, 10 mg/L or greater, and 100 mg/L), or any combination thereof. Preferably, the aldehydes are linear aldehydes that do not have substitutions at the positions alpha or beta to the aldehyde carbonyl group.

Exemplary aldehydes include (CAS numbers provided in parentheses): decanal (112-31-2), 2-methyl decanal (aldehyde c-11 (19009-56-4), 10-undecen-1-al (112-45-8), undecanal (112-44-7), dodecanal (112-54-9), 2-methyl undecanal (110-41-8), heptanal (111-71-7), octanal (124-13-0), green hexanal (5435-64-3), nonanal (124-19-6), undecenal mixture (1337-83-3), (E)-dec-2-enal (25447-70-5), (z)-4-decenal (21662-09-9), (e)-4-decenal (65405-70-1), 9-decenal (39770-05-3), isovalerianic aldehyde (590-86-3), amyl cinnamic aldehyde 122-40-7), methyl cinnamic aldehyde (101-39-3), methyl phenyl hexenal (21834-92-4), phenyl propionic aldehyde (104-53-0), para tolyl aldehyde (104-87-0), para anisaldehyde (123-11-5), benzaldehyde (100-52-7), 2,4-ivy carbaldehyde (Ald AA triplal, 68039-49-6), tricyclal (68039-49-6), cyclomyral (68738-94-3), is ocyclocitral (1335-66-6), maceal (68259-31-4), safranal (116-26-7), heliotropine (120-57-0), bourgeonal (18127-01-0), cinnamic aldehyde (104-55-2), cuminic aldehyde (122-03-2), cyclamen aldehyde (103-95-7), cyclohexal (31906-04-4), fennaldehyde (5462-06-6), floralozone (67634-15-5), florhydral (125109-85-5), hydratropic aldehyde (93-53-8), mefranal (55066-49-4), myraldene (37677-14-8), silvial (6658-48-6), trifernal (16251-77-7), 2-tridecenal (7774-82-5), dupical (30168-23-1), scentenal (86803-90-9), precyclemone b (52475-86-2), vernaldehyde (66327-54-6), hexanal (66-25-1), adoxal (141-13-9), calypsone (929253-05-4), cetonal (65405-84-7), citral (5392-40-5), citronellal (106-23-0), citronellyl oxyacetaldehyde (7492-67-3), dihydro farnesal (32480-08-3), hydroxycitronellal (107-75-5), melonal (106-72-9), methoxymelonal (62439-41-2), nonadienal (557-48-2), oncidal (54082-68-7), pinoacetaldehyde (33885-51-7), tetrahydro citral (5988-91-0), tropional (1205-17-0), ethyl vanillin (121-32-4), vanillin (121-33-5), *magnolia* decadienal (Floral super, 71077-31-1), melozone (30772-79-3), 3-(p-cumenyl)propionaldehyde (Cyclemax, 7775-00-0), (E)-2-dodecenal (20407-84-5) and any combinations thereof.

The microcapsule compositions of the invention can also encapsulate one or more other active materials including, but not limited to, those listed in WO 2016049456, pages 38-50. These active materials include flavor ingredients, taste masking agents, taste sensates, malodor counteracting agents, vitamins or derivatives thereof, antibacterials, sunscreen actives, antioxidants, anti-inflammatory agents, fungicide, anesthetics, analgesics, antifungal agents, antibiotics, anti-viral agents, anti-parasitic agents, anti-infectious, anti-acne agents, dermatological active ingredients, enzymes and co-enzymes, skin whitening agents, anti-histamines, chemotherapeutic agents, insect repellents, emollient, skin moisturizing agent, wrinkle control agent, UV protection agent, fabric softener active, hard surface cleaning active, skin or hair conditioning agent, animal repellent, vermin repellent, flame retardant, antistatic agent, nanometer to micron size inorganic solid, polymeric or elastomeric particle, and combination thereof.

In addition to the active materials listed above, the microcapsule compositions of this invention can also contain, for example, the following dyes, colorants or pigments: lactoflavin (riboflavin), beta-carotene, riboflavin-5'-phosphate, alpha-carotene, gamma-carotene, cantaxanthin, erythrosine, curcumin, quinoline yellow, yellow orange S, tartrazine, bixin, norbixin (annatto, orlean), capsanthin, capsorubin, lycopene, beta-apo-8'-carotenal, beta-apo-8'-carotenic acid ethyl ester, xantophylls (flavoxanthin, lutein, cryptoxanthin, rubixanthin, violaxanthin, rodoxanthin), fast carmine (carminic acid, cochineal), azorubin, cochineal red A (Ponceau 4 R), beetroot red, betanin, anthocyanins, amaranth, patent blue V, indigotine I (indigo-carmine), chlorophylls, copper compounds of chlorophylls, acid brilliant green BS (lissamine green), brilliant black BN, vegetable carbon, titanium dioxide, iron oxides and hydroxides, calcium carbonate, aluminum, silver, gold, pigment rubine BK (lithol rubine BK), methyl violet B, victoria blue R, victoria blue B, acilan brilliant blue FFR (brilliant wool blue FFR), naphthol green B, acilan fast green 10 G (alkali fast green 10 G), ceres yellow GRN, sudan blue II, ultramarine, phthalocyanine blue, phthalocayanine green, fast acid violet R. Further naturally obtained extracts (for example paprika extract, black carrot extract, red cabbage extract) can be used for coloring purposes. Goods results are also achieved with the colors named in the following, the so-called aluminum lakes: FD & C Yellow 5 Lake, FD & C Blue 2 Lake, FD & C Blue 1 Lake, Tartrazine Lake, Quinoline Yellow Lake, FD & C Yellow 6 Lake, FD & C Red 40 Lake, Sunset Yellow Lake, Carmoisine Lake, Amaranth Lake, Ponceau 4R Lake, Erythrosyne Lake, Red 2G Lake, Allura Red Lake, Patent Blue V Lake, Indigo Carmine Lake, Brilliant Blue Lake, Brown HT Lake, Black PN Lake, Green S Lake and mixtures thereof.

When the active material is a fragrance, it is preferred that fragrance ingredients within a fragrance having a C log P of 0.5 to 15 are employed. For instance, the ingredients having a C log P value between 0.5 to 8 (e.g., between 1 to 12, between 1.5 to 8, between 2 and 7, between 1 and 6, between 2 and 6, between 2 and 5, between 3 and 7) are 25% or greater (e.g., 50% or greater and 90% or greater) by the weight of the fragrance.

It is preferred that a fragrance having a weight-averaged C log P of 2.5 and greater (e.g., 3 or greater, 2.5 to 7, and 2.5 to 5) is employed. The weight-averaged C log P is calculated as follows:

$$C \log P = \{\text{Sum}[(Wi)(C \log P)i]\}/\{\text{Sum } Wi\},$$

in which Wi is the weight fraction of each fragrance ingredient and (C log P)i is the C log P of that fragrance ingredient.

As an illustration, it is preferred that greater than 60 wt % (preferably greater than 80 wt % and more preferably greater than 90 wt %) of the fragrance chemicals have C log P values of greater than 2 (preferably greater than 3.3, more preferably greater than 4, and even more preferably greater than 4.5).

Those with skill in the art will appreciate that many fragrances can be created employing various solvents and fragrance chemicals. The use of a relatively low to intermediate C log P fragrance ingredients will result in fragrances that are suitable for encapsulation. These fragrances are generally water-insoluble, to be delivered through the capsule systems of this invention onto consumer products in different stages such as damp and dry fabric. Without encapsulation, the free fragrances would normally have evaporated or dissolved in water during use, e.g., wash. Though high C log P materials are generally well delivered from a regular (non-encapsulated) fragrance in a consumer product, they have excellent encapsulation properties and are also suitable for encapsulation for overall fragrance character purposes, very long-lasting fragrance delivery, or overcoming incompatibility with the consumer product, e.g., fragrance materials that would otherwise be instable, cause thickening or discoloration of the product or otherwise negatively affect desired consumer product properties.

In some embodiments, the amount of encapsulated active material is from 5% to 95% (e.g., 10% to 90%, 15% to 80%, and 20% to 60%) by weight of the microcapsule composition. The amount of the capsule wall is from 0.5% to 30% (e.g., 1% to 25%, 2 to 20% and 5 to 15%) also by weight of the microcapsule composition. In other embodiments, the amount of the encapsulated active material is from 15% to 99.5% (e.g., 20% to 98% and 30% to 90%) by weight of the microcapsule, and the amount of the capsule wall is from 0.5% to 85% (e.g., 2 to 50% and 5 to 40%) by weight of the microcapsule.

Adjunct Materials

In addition to the active materials, the present invention also contemplates the incorporation of adjunct materials including solvent, emollients, and core modifier materials in the core encapsulated by the capsule wall. Other adjunct materials are solubility modifiers, density modifiers, stabilizers, viscosity modifiers, pH modifiers, or any combination thereof. These modifiers can be present in the wall or core of the capsules, or outside the capsules in delivery system. Preferably, they are in the core as a core modifier.

The one or more adjunct material may be added in the amount of 0.01% to 40% (e.g., 0.5% to 30%) by weight of the microcapsule.

Suitable examples include those described in WO 2016/049456, pages 55-57 and US 2016/0158121, pages 15-18.

Deposition Aids

An exemplary deposition aid useful in the microcapsule composition of this invention is a copolymer of acrylamide and acrylamidopropyltrimonium chloride. This copolymer facilitates the deposition of the microcapsule onto a hard surface (e.g., hair, skin, fiber, furniture, and floor). The copolymer generally has an average molecular weight (e.g., weight average molecular mass (Mw) determined by size exclusion chromatography) of 2,000 Daltons to 10,000,000 Daltons with a lower limit of 2,000, 5,000, 10,000, 20,000, 50,000, 100,000, 250,000, 500,000, or 800,000 Daltons and an upper limit of 10,000,000, 5,000,000, 2,000,000, 1,000,000, or 500,000 Daltons (e.g., 500,000 to 2,000,000 and 800,000 to 1,500,000 Daltons). The charge density of the copolymer ranges from 1 meq/g to 2.5 meq/g, preferably from 1.5 to 2.2 meq/g. The copolymer of acrylamide and acrylamidopropyltrimonium chloride is commercially available from various vendors such as Ashland as N-Hance® SP-100 and Ciba SALCARE® SC60.

Other suitable deposition aids include anionically, cationically, nonionically, or amphoteric water-soluble polymers. Suitable deposition aids include polyquaternium-4, polyquaternium-5, polyquaternium-6, polyquaternium-7, polyquaternium-10, polyquaternium-11, polyquaternium-16, polyquaternium-22, polyquaternium-24, polyquaternium-28, polyquaternium-37, polyquaternium-39, polyquaternium-44, polyquaternium-46, polyquaternium-47, polyquaternium-53, polyquaternium-55, polyquaternium-67, polyquaternium-68, polyquaternium-69, polyquaternium-73, polyquaternium-74, polyquaternium-77, polyquaternium-78, polyquaternium-79, polyquaternium-79/hydrolyzed keratin, polyquaternium-80, polyquaternium-81, polyquaternium-82, polyquaternium-86, polyquaternium-88, polyquaternium-101, polyvinylamine, polyethyleneimine, a copolymer of vinylamine and vinylformamide, methacrylamidopropyl trimethyl ammonium polymer, polyacrylamide, polyacrylic acid, dimethyl ammonium polymer, polyvinylformamide, polyvinylpyrollidone, polyvinylalcohol, a copolymer of acrylamide and 3-methacryloylaminopropyl trimethylammonium, a 3-acrylamidopropyl trimethylammonium polymer or its copolymer, a diallyldimethylammoniumchloride polymer and its copolymer, a polysaccharide with saccharide unit functionalized with hydroxypropyl trimmonium, ethyltrimonium chloride methacrylate/hydrolyzed wheat protein copolymer, alkylmonium hydroxypropyl hydrolyzed protein, xylose, galactose, hydroxypropylated glucose, hydroxyethylated glucose, hydroxymethylated glucose, functionalized branched polyethylenimine, caprolactone, catechol, hydroxypropylcellulose, polymer comprising units derived from polyethylene glycol and terephthalate, and combinations thereof. More examples of the deposition aid are described in WO 2016/049456, pages 13-27; US 2013/0330292; US 2013/0337023; and US 2014/0017278.

Additional depositional aids are those cationic polymers described in WO2016/032993. These cationic polymers are typically characterized by a relatively high charge density (e.g., from 4 meq/g, or from 5 meq/g, or from 5.2 meq/g to 12 meq/g, or to 10 meq/g, or to 8 meq/g or to 7 meq/g, or to 6.5 meq/g. The cationic polymers are comprised of structural units that are nonionic, cationic, anionic, or mixtures thereof. In some aspects, the cationic polymer comprises from 5 mol % to 60 mol %, or from 15 mol % to 30 mol %, of a nonionic structural unit derived from a monomer selected from the group consisting of (meth)acrylamide, vinyl formamide, N,N-dialkyl acrylamide, N,N-dialkyl-methacrylamide, $C_1$-$C_{12}$ alkyl acrylate, $C_1$-$C_{12}$ hydroxyalkyl acrylate, polyalkylene glyol acrylate, $C_1$-$C_{12}$ alkyl methacrylate, $C_1$-$C_{12}$ hydroxyalkyl methacrylate, polyalkylene glycol methacrylate, vinyl acetate, vinyl alcohol, vinyl formamide, vinyl acetamide, vinyl alkyl ether, vinyl pyridine, vinyl pyrrolidone, vinyl imidazole, vinyl caprolactam, and mixtures thereof.

In some aspects, the cationic polymer comprises a cationic structural unit at the level of 30 mol % to 100 mol %, or 50 mol % to 100 mol %, or 55 mol % to 95 mol %, or 70 mol % to 85 mol % by mass of the cationic polymer. The cationic structural unit is typically derived from a cationic monomer such as N,N-dialkylaminoalkyl methacrylate, N,N-dialkylaminoalkyl acrylate, N,N-dialkylaminoalkyl acrylamide, N,N-dialkylaminoalkylmethacrylamide, methacylamidoalkyl trialkylammonium salts, acrylamidoalkyll-trialkylamminium salts, vinylamine, vinylimine, vinyl imidazole, quaternized vinyl imidazole, diallyl dialkyl ammonium salts, and mixtures thereof. Preferably, the cationic monomer is selected from the group consisting of diallyl dimethyl ammonium salts (DADMAS), N,N-dimethyl aminoethyl acrylate, N,N-dimethyl aminoethyl methacrylate (DMAM), [2-(methacryloylamino)ethyl]tri-methylammonium salts, N,N-dimethylaminopropyl acrylamide (DMAPA), N,N-dimethylaminopropyl methacrylamide (DMAPMA), acrylamidopropyl trimethyl ammonium salts (APTAS), methacrylamidopropyl trimethylammonium salts (MAPTAS), quaternized vinylimidazole (QVi), and mixtures thereof.

In some aspects, the cationic polymer comprises an anionic structural unit at a level of 0.01 mol % to 15 mol %, 0.05 mol % to 10 mol %, 0.1 mol % to 5 mol %, or 1% to 4% of by mass of the cationic polymer. In some aspects, the anionic structural unit is derived from an anionic monomer selected from the group consisting of acrylic acid (AA), methacrylic acid, maleic acid, vinyl sulfonic acid, styrene sulfonic acid, acrylamidopropylmethane sulfonic acid (AMPS) and their salts, and mixtures thereof.

Exemplary cationic polymers include polyacrylamide-co-DADMAS, polyacrylamide-co-DADMAS-co-acrylic acid, polyacrylamide-co-APTAS, polyacrylamide-co-MAPTAS, polyacrylamide-co-QVi, polyvinyl formamide-co-DADMAS, poly(DADMAS), polyacrylamide-co-MAPTAS-coacrylic acid, polyacrylamide-co-APTAS-co-acrylic acid, and mixtures thereof.

The deposition aid is generally present at a level of 0.01% to 50% (with a lower limit of 0.01%, 0.05%, 0.1%, 0.5%, 1%, 2%, or 5% and an upper limit of 50%, 40%, 30%, 20%, 15%, or 10%, e.g., 0.1% to 30%, 1% to 20%, 2% to 15%, and 5% to 10%) by weight of the microcapsule composition. In a consumer product such as a shampoo, the deposition aid is generally present at a level of 0.001% to 20% (with a lower limit of 0.001%, 0.005%, 0.01%, 0.02%, or 0.05% and an upper limit of 20%, 15%, 10%, 5%, 2%, or 1%, e.g., 0.005% to 10%, 0.01% to 5%, and 0.02% to 0.5%) by weight of the shampoo composition. The capsule deposition aid can be added during the preparation of the microcapsules or it can be added after the microcapsules have been made.

A second capsule deposition aid from 0.01% to 25%, more preferably from 5% to 20% can be added to the microcapsule composition. The second capsule formation deposition aid can be selected from the above-described deposition aid.

Additional Components

The microcapsule composition of this invention can include one or more non-confined or unencapsulated active materials from 0.01 to 50%, more preferably from 5 to 40%.

The capsule delivery system can also contain one or more other delivery system such as polymer-assisted delivery compositions (see U.S. Pat. No. 8,187,580), fiber-assisted delivery compositions (US 2010/0305021), cyclodextrin host guest complexes (U.S. Pat. No. 6,287,603 and US 2002/0019369), pro-fragrances (WO 2000/072816 and EP 0 922 084), and any combination thereof. More exemplary delivery systems that can be incorporated are coacervate capsules, cyclodextrin delivery systems, and pro-perfumes.

Examples of additional components include those described in US 2016/0158121.

Any compound, polymer, or agent discussed above can be the compound, polymer, or agent itself as shown above, or its salt, precursor, hydrate, or solvate. A salt can be formed between an anion and a positively charged group on the compound, polymer, or agent. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group on the compound, polymer, or agent. Suitable cations include sodium ion, potassium ion, magnesium ion, calcium ion, and an ammonium cation (e.g., tetramethylammonium ion). A precursor can be ester and another suitable derivative, which, during the process of preparing a polyurea or polyurethane capsule composition of this invention, is capable of converting to the compound, polymer, or agent and being used in preparing the polyurea or polyurethane capsule composition. A hydrate refers to the compound, polymer, or agent that contains water. A solvate refers to a complex formed between the compound, polymer, or agent and a suitable solvent. A suitable solvent can be water, ethanol, isopropanol, ethyl acetate, acetic acid, and ethanolamine.

Certain compounds, polymers, and agents have one or more stereocenters, each of which can be in the R configuration, the S configuration, or a mixture. Further, some compounds, polymers, and agents possess one or more double bonds wherein each double bond exists in the E (trans) or Z (cis) configuration, or combinations thereof. The compounds, polymers, and agents include all possible configurational stereoisomeric, regioisomeric, diastereomeric, enantiomeric, and epimeric forms as well as any mixtures thereof. As such, lysine used herein includes L-lysine, D-lysine, L-lysine monohydrochloride, D-lysine monohydrochloride, lysine carbonate, and so on. Similarly, arginine includes L-arginine, D-arginine, L-arginine monohydrochloride, D-arginine monohydrochloride, arginine carbonate, arginine monohydrate, and etc. Guanidine includes guanidine hydrochloride, guanidine carbonate, guanidine thiocyanate, and other guanidine salts including their hydrates. Ornithine includes L-ornithine and its salts/hydrates (e.g., monohydrochloride) and D-ornithine and its salts/hydrates (e.g., monohydrochloride).

The microcapsule composition of this invention can be a slurry containing the capsule at a level 0.1% to 80% with a lower limit of 0.1%, 0.5%, 1%, 5%, 10%, 15%, 20%, 25%, 30%, 35%, 40%, 45%, 50%, 55%, 60%, or 65% and an upper limit of 80%, 75%, 70%, 65%, 60%, 55%, 50%, 45%, 40%, or 35% (preferably 10% to 65% and more preferably 35 to 55%) by weight of the capsule composition. In the slurry, the capsule is suspended in an aqueous phase. An exemplary microcapsule composition of this invention contains a plurality of microcapsules each dispersed in an aqueous phase and is stable for at least 7 days (e.g., at least 10 days, at least 30 days, and at least 60 days) at the temperature of 40° C. Stability is measured (e.g., in a graduated cylinder) by the separation of a clear aqueous phase from the microcapsule composition. The microcapsule composition is deemed stable if, by volume of the microcapsule composition, less than 10% of a clear aqueous phase is separated. The microcapsule composition is considered stable when (i) the composition has a viscosity of 3000 cP or less (e.g., 2000 cP or less) and (ii) 20% or less (e.g., 15% or less, and 10% or less) water by volume of the composition is separated from the composition. The volume of the separated water can be readily measured by a convention method, e.g., a graduated cylinder.

Microcapsule compositions are known to have the tendency to form into gels, unsuitable for use in many consumer products. The viscosity of the gelled-out composition increases to at least 3000 centipoise (cP) (e.g., at least 6000 cP). The viscosity can be readily measured on rheometer, for example a RheoStress™ 1 instrument (Commercially available from ThermoScientific), using rotating disks at a shear rate of 21 Hertz ($s^{-1}$) and a temperature of 25° C. The viscosity can also be measured at a shear rate of 2 $s^{-1}$, 106 $s^{-1}$, or any other shear rate suitable for the material and instrument.

In some embodiments, the microcapsule composition is purified by washing the capsule slurry with water until a neutral pH (pH of 6 to 8) is achieved. For the purposes of the present invention, the capsule suspension can be washed using any conventional method including the use of a separatory funnel, filter paper, centrifugation and the like. The capsule suspension can be washed one, two, three, four, five, six, or more times until a neutral pH, e.g., pH 6-8 and 6.5-7.5, is achieved. The pH of the purified capsules can be determined using any conventional method including, but not limited to pH paper, pH indicators, or a pH meter.

A capsule composition is "purified" in that it is 80%, 90%, 95%, 97%, 98% or 99% homogeneous to capsules. In accordance with the present invention, purity is achieved by washing the capsules until a neutral pH is achieved, which is indicative of removal of unwanted impurities and/or starting materials, e.g., polyisocyanate, cross-linking agent and the like.

In certain embodiments of this invention, the purification of the capsules includes the additional step of adding a salt to the capsule suspension prior to the step of washing the capsule suspension with water. Exemplary salts of use in this step of the invention include, but are not limited to, sodium chloride, potassium chloride or bi-sulphite salts. See US 2014/0017287.

The microcapsule composition of this invention can also dried, e.g., spray dried, heat dried, and belt dried, to a solid form. In a spray drying process, a spray dry carrier is added to a microcapsule composition to assist the removal of water from the slurry. See US2012/0151790, US2014/0377446, US2015/0267964, US2015/0284189, and US2016/0097591.

According to one embodiment, the spray dry carriers can be selected from the group consisting of carbohydrates such as chemically modified starches and/or hydrolyzed starches, gums such as gum arabic, proteins such as whey protein, cellulose derivatives, clays, synthetic water-soluble polymers and/or copolymers such as polyvinyl pyrrolidone, polyvinyl alcohol. The spray dry carriers may be present in an amount from 1 to 50%, more preferably from 5 to 20%, by weight of the microcapsule composition in slurry.

Optionally, a free flow agent (anticaking agent) of silicas which may be hydrophobic (i.e. silanol surface treated with halogen silanes, alkoxysilanes, silazanes, siloxanes, etc. such as Sipernat® D17, Aerosil® R972 and R974 (available from Degussa), etc.) and/or hydrophilic such as Aerosil® 200, Sipernat® 22S, Sipernat® 505, (available from Degussa), Syloid® 244 (available from Grace Davison), may be present from 0.01 to 10%, more preferable from 0.5 to 5%, by weight of the microcapsule composition in slurry.

Humectants and viscosity control/suspending agents can also be added to facilitate spray drying. These agents are disclosed in U.S. Pat. Nos. 4,446,032 and 6,930,078. Details of hydrophobic silica as a functional delivery vehicle of active materials other than a free flow/anticaking agent are disclosed in U.S. Pat. Nos. 5,500,223 and 6,608,017.

The spray drying inlet temperature is in the range of 150 to 240° C., preferably between 17° and 230° C., more preferably between 19° and 220° C.

As described herein, the spray-dried microcapsule composition is well suited for use in a variety of all dry (anhydrous) products: powder laundry detergent, fabric softener dryer sheets, household cleaning dry wipes, powder dish detergent, floor cleaning cloths, or any dry form of personal care products (e.g. shampoo powder, deodorant powder, foot powder, soap powder, baby powder), etc. Because of high fragrance and/or active agent concentration in the spray-dried products of the present invention, characteristics of the aforementioned consumer dry products will not be adversely affected by a small dosage of the spray-dried products.

The microcapsule composition can also be sprayed as a slurry onto a consumer product, e.g., a fabric care product. By way of illustration, a liquid delivery system containing capsules is sprayed onto a detergent powder during blending to make granules. See US 2011/0190191. In order to increase fragrance load, water-absorbing material, such as zeolite, can be added to the delivery system.

Alternatively, granulates in a consumer product are prepared in a mechanical granulator in the presence of a granulation auxiliary such as non-acid water-soluble organic crystalline solids. See WO 2005/097962.

Zeta Potentials and Rupture Forces

The microcapsule of this invention is positively charged as indicated by a zeta potential of at least 10 mV, preferably at least 25 mV (e.g., 25 to 200 mV), and more preferably at least 40 mV (e.g., 40 to 100 mV).

Zeta potential is a measurement of electrokinetic potential in the microcapsule. From a theoretical viewpoint, zeta potential is the potential difference between the water phase (i.e., the dispersion medium) and the stationary layer of water attached to the surface of the microcapsule.

The zeta potential is an important indicator of the stability of the microcapsule in compositions or consumer products. Typically, a microcapsule having a zeta potential of 10 to 25 mV shows a moderate stability. Similarly, a microcapsule having a zeta potential of 25 to 40 mV shows a good stability and a microcapsule having a zeta potential of 40 to 100 mV shows excellent stability. Not to be bound by any theory, the microcapsule of this invention has a desirable zeta potential making it suitable for use in consumer products with improved stability.

The zeta potential can be calculated using theoretical models and an experimentally-determined electrophoretic mobility or dynamic electrophoretic mobility. The zeta potential is conventionally measured by methods such as microelectrophoresis, or electrophoretic light scattering, or electroacoustic phenomena. For more detailed discussion on measurement of zeta potential, see Dukhin and Goetz, "Ultrasound for characterizing colloids", Elsevier, 2002.

The microcapsule of this invention has a fracture strength of 0.2 to 80 MPa (e.g., 0.5 to 60 MPa, 1 to 50 MPa, and 5 to 30 MPa). The fracture strength of each microcapsule is calculated by dividing the rupture force (in Newtons) by the cross-sectional area of the respective microcapsule ($\pi r^2$, where r is the radius of the particle before compression). The measurement of the rupture force and the cross-sectional area is performed following the methods described in Zhang et al., *J. Microencapsulation* 18(5), 593-602 (2001).

The microcapsule of this invention has a rupture force of less than 10 millinewtons ("mN") such as 0.1 mN to 10 mN, 0.2 mN to 8 mN, 0.3 mN to 5 mN, 0.1 mN to 2 mN, 0.1 mN, 0.5 mN, 1 mN, 2 mN, 5 mN, and 8 mN. The rupture force is the force needed to rupture the microcapsules. Its measurement is based on a technique known in the art as micro-manipulation. See Zhang et al., *Journal of Microencapsulation* 16(1), 117-124 (1999).

Applications

The microcapsule of the present invention is well-suited for use, without limitation, in the following additional products:

a) Household products i. Liquid or Powder Laundry Detergents which can use the present invention include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818 ii. Unit Dose Pouches, Tablets and Capsules such as those described in EP 1 431 382 A1, US 2013/0219996 A1, US 2013/0284637 A1, and U.S. Pat. No. 6,492,315. These unit dose formulations can contain high concentrations of a functional material (e.g., 5-100% fabric softening agent or detergent active), fragrance (e.g., 0.5-100%, 0.5-40%, and 0.5-15%), and flavor (e.g., 0.1-100%, 0.1-40%, and 1-20%). They can contain no water to limit the water content as low as less than 30% (e.g., less than 20%, less than 10%, and less than 5%).

iii. Scent Boosters such as those described in U.S. Pat. Nos. 7,867,968, 7,871,976, 8,333,289, US 2007/0269651 A1, and US2014/0107010 A1.

iv. Fabric Care Products such as Rinse Conditioners (containing 1-30 weight % of a fabric conditioning active), Fabric Liquid Conditioners (containing 1 to 30 weight % of a fabric conditioning active), Tumble Drier Sheets, Fabric Refreshers, Fabric Refresher Sprays, Ironing Liquids, and Fabric Softener Systems such as those described in U.S. Pat. Nos. 6,335,315, 5,674,832, 5,759,990, 5,877,145, 5,574,179, 5,562,849, 5,545,350, 5,545,340, 5,411,671, 5,403,499, 5,288,417, 4,767,547 and 4,424,134 Liquid fabric softeners/fresheners contain at least one fabric softening agent present, preferably at a concentration of 1 to 30% (e.g., 4 to 20%, 4 to 10%, and 8 to 15%). The ratio between the active material and the fabric softening agent can be 1:500 to 1:2 (e.g., 1:250 to 1:4 and 1:100 to 1:8). As an illustration, when the fabric softening agent is 5% by weight of the fabric softener, the active material is 0.01 to 2.5%, preferably 0.02 to 1.25% and more preferably 0.1 to 0.63%. As another example, when the fabric softening agent is 20% by weight of the fabric softener, the active material is 0.04 to 10%, preferably 0.08 to 5% and more preferably 0.4 to 2.5%. The active material is a fragrance, malodor counteractant or mixture thereof. The liquid fabric softener can have 0.15 to 15% of capsules (e.g., 0.5 to 10%, 0.7 to 5%, and 1 to 3%). When including capsules at these levels, the neat oil equivalent (NOE) in the softener is 0.05 to 5% (e.g., 0.15 to 3.2%, 0.25 to 2%, and 0.3 to 1%).

Suitable fabric softening agents include cationic surfactants. Non-limiting examples are quaternary ammonium compounds such as alkylated quaternary ammonium compounds, ring or cyclic quaternary ammonium compounds, aromatic quaternary ammonium compounds, diquaternary ammonium compounds, alkoxylated quaternary ammonium compounds, amidoamine quaternary ammonium compounds, ester quaternary ammonium compounds, and mixtures thereof. Fabric softening compositions, and components thereof, are generally described in US 2004/0204337 and US 2003/0060390. Suitable softening agents include esterquats such as Rewoquat WE 18 commercially available from Evonik Industries and Stepantex SP-90 commercially available from Stepan Company.
v. Liquid dish detergents such as those described in U.S. Pat. Nos. 6,069,122 and 5,990,065
vi. Automatic Dish Detergents such as those described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562
vii. All-purpose Cleaners including bucket dilutable cleaners and toilet cleaners
viii. Bathroom Cleaners
ix. Bath Tissue
x. Rug Deodorizers
xi. Candles
xii. Room Deodorizers
xiii. Floor Cleaners
xiv. Disinfectants
xv. Window Cleaners
xvi. Garbage bags/trash can liners
xvii. Air Fresheners including room deodorizer and car deodorizer, scented candles, sprays, scented oil air freshener, Automatic spray air freshener, and neutralizing gel beads
xviii. Moisture absorber
xix. Household Devices such as paper towels and disposable Wipes
xx. Moth balls/traps/cakes
b) Baby Care Products
 i. Diaper Rash Cream/Balm
 ii. Baby Powder
c) Baby Care Devices
 i. Diapers
 ii. Bibs
 iii. Wipes
d) Oral Care Products. Tooth care products (as an example of preparations according to the invention used for oral care) generally include an abrasive system (abrasive or polishing agent), for example silicic acids, calcium carbonates, calcium phosphates, aluminum oxides and/or hydroxylapatites, surface-active substances, for example sodium lauryl sulfate, sodium lauryl sarcosinate and/or cocamidopropylbetaine, humectants, for example glycerol and/or sorbitol, thickening agents, for example carboxymethyl cellulose, polyethylene glycols, carrageenan and/or Laponite®, sweeteners, for example saccharin, taste correctors for unpleasant taste sensations, taste correctors for further, normally not unpleasant taste sensations, taste-modulating substances (for example inositol phosphate, nucleotides such as guanosine monophosphate, adenosine monophosphate or other substances such as sodium glutamate or 2-phenoxypropionic acid), cooling active ingredients, for example menthol derivatives, (for example L-menthyllactate, L-menthylalkylcarbonates, menthone ketals, menthane carboxylic acid amides), 2,2,2-trialkylacetic acid amides (for example 2,2-diisopropylpropionic acid methyl amide), icilin and icilin derivatives, stabilizers and active ingredients, for example sodium fluoride, sodium monofluorophosphate, tin difluoride, quaternary ammonium fluorides, zinc citrate, zinc sulfate, tin pyrophosphate, tin dichloride, mixtures of various pyrophosphates, triclosan, cetylpyridinium chloride, aluminum lactate, potassium citrate, potassium nitrate, potassium chloride, strontium chloride, hydrogen peroxide, flavorings and/or sodium bicarbonate or taste correctors.
 i. Tooth Paste. An exemplary formulation as follows:
  1. calcium phosphate 40-55%
  2. carboxymethyl cellulose 0.8-1.2%
  3. sodium lauryl sulfate 1.5-2.5%
  4. glycerol 20-30%
  5. saccharin 0.1-0.3%
  6. flavor oil 1-2.5%
  7. water q.s. to 100%
   A typical procedure for preparing the formulation includes the steps of (i) mixing by a blender according to the foregoing formulation to provide a toothpaste, and (ii) adding a composition of this invention and blending the resultant mixture till homogeneous.
 ii. Tooth Powder
 iii. Oral Rinse
 iv. Tooth Whiteners
 v. Denture Adhesive
e) Health Care Devices
 i. Dental Floss
 ii. Toothbrushes
 iii. Respirators
 iv. Scented/flavored condoms
f) Feminine Hygiene Products such as Tampons, Feminine Napkins and Wipes, and Pantiliners
g) Personal Care Products: Cosmetic or pharmaceutical preparations, e.g., a "water-in-oil" (W/O) type emulsion, an "oil-in-water" (O/W) type emulsion or as multiple emulsions, for example of the water-in-oil-in-water (W/O/W) type, as a PIT emulsion, a Pickering emulsion, a micro-emulsion or nano-emulsion; and emulsions which are particularly preferred are of the "oil-in-water" (O/W) type or water-in-oil-in-water (W/O/W) type. More specifically,
 i. Personal Cleansers (bar soaps, body washes, and shower gels)
 ii. In-shower conditioner
 iii. Sunscreen ant tattoo color protection (sprays, lotions, and sticks)
 iv. Insect repellants
 v. Hand Sanitizer
 vi. Antiinflammatory balms, ointments, and sprays
 vii. Antibacterial ointments and creams
 viii. Sensates
 ix. Deodorants and Antiperspirants including aerosol and pump spray antiperspirant, stick antiperspirant, roll-on antiperspirant, emulsion spray antiperspirant, clear emulsion stick antiperspirant, soft solid antiperspirant, emulsion roll-on antiperspirant, clear emulsion stick antiperspirant, opaque emulsion stick antiperspirant, clear gel antiperspirant, clear stick deodorant, gel deodorant, spray deodorant, roll-on, and cream deodorant
 x. Wax-based Deodorant. An exemplary formulation as follows:
  1. Paraffin Wax 10-20%
  2. Hydrocarbon Wax 5-10%
  3. White Petrolatum 10-15%
  4. Acetylated Lanolin Alcohol 2-4%
  5. Diisopropyl Adipate 4-8%
  6. Mineral Oil 40-60%
  7. Preservative (as needed)

The formulation is prepared by (i) mixing the above ingredients, (ii) heating the resultant composition to 75° C. until melted, (iii) with stirring, adding 4% cryogenically ground polymer containing a fragrance while maintaining the temperature 75° C., and (iv) stirring the resulting mixture in order to ensure a uniform suspension while a composition of this invention is added to the formulation.

xi. Glycol/Soap Type Deodorant. An exemplary formulation as follows:
1. Propylene Glycol 60-70%
2. Sodium Stearate 5-10%
3. Distilled Water 20-30% 4.2,4,4-Trichloro-2'-Hydroxy Diphenyl Ether, manufactured by the Ciba-Geigy
   Chemical Company and a Trademark of the Ciba-Geigy Chemical Company) 0.01-0.5%
   The ingredients are combined and heated to 75° C. with stirring until the sodium stearate has dissolved. The resulting mixture is cooled to 40° C. followed by addition of a composition of this invention.

xii. Lotion including body lotion, facial lotion, and hand lotion
xiii. Body powder and foot powder
xiv. Toiletries
xv. Body Spray
xvi. Shave cream and male grooming products
xvii. Bath Soak
xviii. Exfoliating Scrub h) Personal Care Devices
   i. Facial Tissues
   ii. Cleansing wipes i) Hair Care Products
   i. Shampoos (liquid and dry powder)
   ii. Hair Conditioners (Rinse-out conditioners, leave-in conditioners, and cleansing conditioners)
   iii. Hair Rinses
   iv. Hair Refreshers
   v. Hair perfumes
   vi. Hair straightening products
   vii. Hair styling products, Hair Fixative and styling aids
   viii. Hair combing creams
   ix. Hair wax
   x. Hair foam, hair gel, nonaerosol pump spray
   xi. Hair Bleaches, Dyes and Colorants
   xii. Perming agents
   xiii. Hair wipes j) Beauty Care
   i. Fine Fragrance—Alcoholic. Compositions and methods for incorporating fragrance capsules into alcoholic fine fragrances are described in U.S. Pat. No. 4,428,869. Alcoholic fine fragrances may contain the following:
      1. Ethanol (1-99%)
      2. Water (0-99%)
      3. A suspending aide including but not limited to: hydroxypropyl cellulose, ethyl cellulose, silica, microcrystalline cellulose, carrageenan, propylene glycol alginate, methyl cellulose, sodium carboxymethyl cellulose or xanthan gum (0.1%)
      4. Optionally an emulsifier or an emollient may be included including but not limited to those listed above
   ii. Solid Perfume
   iii. Lipstick/lip balm
   iv. Make-up cleanser
   v. Skin care cosmetic such as foundation, pack, sunscreen, skin lotion, milky lotion, skin cream, emollients, skin whitening
   vi. Make-up cosmetic including manicure, mascara, eyeliner, eye shadow, liquid foundation, powder foundation, lipstick and cheek rouge k) Consumer goods packaging such as fragranced cartons, fragranced plastic bottles/boxes l) Pet care products
   i. Cat litter
   ii. Flea and tick treatment products
   iii. Pet grooming products
   iv. Pet shampoos
   v. Pet toys, treats, and chewables
   vi. Pet training pads
   vii. Pet carriers and crates Exemplary consumer products include shampoos, hair conditioners, liquid detergents, and fabric conditioner. Their compositions are illustrated below.

Shampoos

A pourable shampoo composition is typically characterized by: (i) a water-based composition that contains water, from 20% to 95% by weight, (ii) a pH range from 3 to 10, preferably from 4 to 8, and (iii) a composition that: contains from 4% to 50%, by weight, of one or more surfactant, anionic, amphoteric, and/or nonionic; may contain from 0.01% to 10%, by weight, of a non-volatile conditioning agent; may contain from 0.02% to 5%, by weight of the composition, of at least one cationic polymer; may contain from 0.005% to 1.5%, by weight, of a polyalkylene glycol; and may contain other optional ingredients.

The shampoo composition can contain the microcapsule composition of this invention at a level of 0.01% to 5% (e.g., 0.02% to 3%, 0.05% to 2%, 0.07%, 0.2%, 0.5%, and 1%), and optionally a free fragrance that is not encapsulated at a level of 0.01% to 5% (e.g., 0.02% to 2%, 0.05% to 1%, 0.08%, 0.5%, and 1%).

Surfactants: The shampoo composition can comprise from 4% to 50%, of one or more surfactant component suitable for application to the hair. Suitable surfactants include anionic surfactants, non-ionic surfactants, and amphoteric surfactants.

The anionic surfactant is believed to provide cleaning and lather performance to the composition. Examples include (i) sulfates such as the alkyl and alkyl ether sulfates, e.g., ammonium lauryl sulfate, ammonium cocoyl sulfate, potassium lauryl sulfate, potassium cocoyl sulfate, sodium lauryl sulfate, sodium cocoyl sulfate, monoethanolamine lauryl sulfate, monoethanolamine cocoyl sulfate, diethanolamine lauryl sulfate, triethanolamine lauryl sulfate, triethylamine lauryl sulfate, ammonium laureth sulfate, potassium laureth sulfate, sodium laureth sulfate, monoethanolamine laureth sulfate, diethanolamine laureth sulfate, triethanolamine laureth sulfate, triethylamine laureth sulfate, and mixtures thereof, (ii) sulfonates such as olefin sulfonates, alkyl aryl sulfonates (e.g., sodium tridecyl benzene sulfonate, and sodium dodecyl benzene sulfonate), sodium xylene sulfonate, reaction products of fatty acids and isethionic acid, sodium or potassium salts of fatty acid amides of methyl tauride in which the fatty acids are derived from coconut oil or palm kernel oil, succinnates (e.g., disodium N-octadecylsulfosuccinate, disodium lauryl sulfosuccinate, diammonium lauryl sulfosuccinate, tetrasodium N-(1,2-dicarboxyethyl)-N-octadecylsulfosuccinnate, diamyl ester of sodium sulfosuccinic acid, dihexyl ester of sodium sulfosuccinic acid, and dioctyl esters of sodium sulfosuccinic acid), (iii) sarcosinates and sarcosine derivatives such as sodium lauryl sarcosinate, lauryl sarcosine, cocoyl sarcosine, and mixtures thereof.

Amphoteric surfactants suitable for shampoos include, but are not limited to, those surfactants broadly described as derivatives of aliphatic secondary and tertiary amines in which the aliphatic radical can be straight or branched chain and wherein one of the aliphatic substituents contains from 8 to 18 carbon atoms and one contains an anionic water solubilizing group such as carboxy, sulfonate, sulfate, phosphate, or phosphonate.

Zwitterionic surfactants suitable for shampoos include, but are not limited to, those surfactants broadly described as derivatives of aliphatic quaternary ammonium, phosphonium, and sulfonium compounds, in which the aliphatic radicals can be straight or branched chain, and wherein one of the aliphatic substituents contains from 8 to 18 carbon atoms and one contains an anionic group such as carboxy, sulfonate, sulfate, phosphate or phosphonate. Preferred zwitterionic detersive surfactants are the betaines. Non-limiting examples are Cocamidopropyl Betaine, Coco-Betaine, Lauramidopropyl Betaine, Sodium cocoamphodiacetate, and mixtures thereof.

Nonionic surfactants, can be broadly defined as compounds containing a hydrophobic moiety and a nonionic hydrophilic moiety. The most common nonionic surfactants suitable for use in shampoos are those based on ethylene oxide, referred to as ethoxylated surfactants. Non limited classes of nonionic ethoxylated surfactants are: alcohol ethoxylates, alkyl phenol ethoxylates, fatty acid ethoxylates, monoalkaolamide ethoxylates, sorbitan ester ethoxylates, fatty amine ethoxylates and ethylene oxide-propylene oxide copolymers (sometimes referred to as polymeric surfactants), and mixtures thereof. Another suitable nonionics for use in shampoos are those describes as multihydroxy products. Non limited examples are glycol esters, glycerol (and polyglycerol) esters, glucosides (and polyglucosides) and sucrose esters and mixtures thereof. Also suitable for use in the shampoos are amine oxides, sulphinyl surfactants and mixtures thereof, which represent nonionic surfactants with a small head group.

Conditioning agents: The shampoo composition may contain from 0.01% to 10% by weight of the composition, of a conditioning agent. It is believed that the conditioning agent provides improved conditioning benefits to the hair, particularly clean hair feel and wet rinse feel. The conditioning agent comprises a water insoluble, water dispersible, non-volatile, liquid that forms emulsified, liquid particles or are solubilized by the surfactant micelles, in the anionic detersive surfactant component (described above). Suitable conditioning agents for use in the shampoo composition are those conditioning agents characterized generally as silicones (e.g. silicone oils, cationic silicones, silicone gums, high refractive silicones, and silicone resins), organic conditioning oils (e.g. hydrocarbon oils, polyolefins, and fatty esters) or combinations thereof, or those conditioning agents which otherwise form liquid, dispersed, particles in the aqueous surfactant matrix herein. Such conditioning agents should be physically and chemically compatible with the essential components of the composition, and should not impair product stability nor performance. The concentration of the conditioning agent in the shampoo composition should be sufficient to provide the desired conditioning benefits, and as will be apparent to one of ordinary skill in the art. Such concentration can vary with the conditioning agent, the conditioning performance desired, the average size of the conditioning agent particles, the type and concentration of other components, and other like factors. The silicone conditioning agent particles may comprise volatile silicone, non-volatile silicone, or combinations thereof. The silicone conditioning agent particles may comprise a silicone fluid conditioning agent and may also comprise other ingredients, such as a silicone resin to improve silicone fluid deposition efficiency or enhance glossiness of the hair. The concentration of the silicone conditioning agent typically ranges from 0.01% to 10%, by weight of the composition. Non-limiting examples of suitable silicone conditioning agents, are silicon oils, silicon gums, cationic silicons, high refractive index silicones, and mixture thereof. Organic conditioning oils: The conditioning component of the shampoo compositions may also comprise, at least one organic conditioning oil as the conditioning agent, either alone or in combination with other conditioning agents, such as the silicones (described above). The organic conditioning oils suitable for use as the conditioning agent herein are preferably low viscosity, water insoluble, liquids selected from the hydrocarbon oils, fatty esters, and mixtures thereof.

Cationic polymer: The shampoo compositions may comprise from 0.02% to 5% by weight of the composition, of at least one organic, cationic deposition and conditioning polymer suitable for application to the hair or skin. Such cationic polymers should be physically and chemically compatible with the essential components described herein, and should not impair product stability nor performance. Examples of cationic polymers which may be suitably employed in the shampoo compositions herein include, but are not limited to cationic polysaccharides (e.g. cationic cellulose derivatives and cationic guars), copolymers of vinyl monomers, vinyl pyrrolidone copolymers, cationic modified proteins, and certain polymeric quaternary salts.

Polyalkylene glycol: The shampoo compositions may comprise from 0.005% to 1.5%, by weight of the composition, of selected polyalkylene glycols suitable for application to the hair or skin. The selected polyalkylene glycols are believed to provide enhanced lather performance and improved shampoo spreadability to the compositions described herein. They are also are known thickening agents. Such polyalkylene glycols should be physically and chemically compatible with the essential components described herein, and should not impair product stability nor performance. Preferred for use herein are polyethylene glycols, polypropylene glycols, and mixtures thereof. Preferred polyethylene glycols include PEG 7M, PEG 14M, PEG 25M, PEG 90M, and mixtures thereof.

Optional ingredients: The shampoo compositions may, in some embodiments, further comprise additional optional components known or otherwise effective for use in hair care or personal care products. Antidandruff active, suspending agents, hair growth regulating agents, and other optional components are described in detail below.

The shampoo compositions may comprise from 0.1% to 4%, by weight of the composition, of an anti-dandruff active suitable for application to the hair or skin. The anti-dandruff active provides the shampoo compositions with anti-microbial activity. Suitable, non-limiting examples of anti-dandruff particulates include: zinc pyrithione, selenium sulfide, particulate sulfur, piroctone olamine and mixtures thereof.

The shampoo compositions may, in some embodiments, comprise a suspending agent suitable for application to the hair or skin. It is believed that the suspending agent suspends water-insoluble, dispersed materials in the shampoo compositions. Such suspending agent should be physically and chemically compatible with the essential components of the composition, and should not impair product stability nor performance. Examples of suspending agents which may be suitably employed in the shampoo compositions herein include, but are not limited to: acyl derivatives, long chain amine oxides, xanthan gum, and mixtures thereof. Acyl derivative suspending agents include, but are not limited to: glyceryl esters, long chain hydrocarbyls, long chain esters of long chain fatty acids, long chain esters of long chain alkanol amides. Preferred acyl derivative suspending agents for use herein are glyceryl esters, which include $C_{16}$ to $C_{22}$ ethylene glycol esters of fatty acids, particularly, the ethylene glycol stearates, both mono- and di-stearate. Another suitable suspending agent group includes the long chain amine oxides. Non-limiting examples of suitable long chain amine oxides for use as suspending agents herein include the alkyl ($C_{16}$-$C_{22}$) dimethyl amine oxides (e.g. stearyl dimethyl amine oxide). Also suitable for use in the shampoo compositions herein are long chain esters of long chain fatty acids or long chain alkanol amides. Non-limiting examples of long chain include: stearyl stearate, cetyl palmitate, stearamide diethanolamide distearate and stearamide monoethanolamide stearate. Still other suitable suspending agents for use in the shampoo compositions include carboxyvinyl polymers. Preferred among these polymers are the copolymers of acrylic acid crosslinked with polyallylsucrose. Non limited examples of these polymers are those known in the industry (CTFA) as carbomer, acrylates/$C_{10}$-$C_{30}$ alkyl acrylate crosspolymer, and acrylates copolymer. Still other suitable suspending agents may be used in the shampoo compositions, including those that can impart a gel-like viscosity to the composition, such as water soluble or colloidally water soluble polymers like cellulose ethers (e.g., methylcellulose, hydroxybutyl methylcellulose, hydroxypropylcellulose, hydroxypropyl methylcellulose, hydroxyethyl ethylcellulose and hydroxyethylcellulose), guar gum, polyvinyl alcohol, polyvinyl pyrrolidone, hydroxypropyl guar gum, starch and starch derivatives, and other thickeners, viscosity modifiers, gelling agents, and mixtures thereof.

The shampoo composition may also optionally comprise, hair growth regulating agents. Such agents can be chosen from a wide variety of molecules which can function in different ways to enhance the hair growth effects of a compound of the present invention. As used herein, the term "hair growth regulating" is meant to include: stimulating hair growth and/or hair thickening; preventing, reducing, arresting and/or retarding the loss of hair and/or the thinning of hair; increasing the rate of hair growth; inducing the formation of a greater number of hair strands; increasing the diameter of the hair strand; lengthening the hair strand; and any combination thereof.

The shampoo composition can also contain other minor components. As used herein, "minor" refers to those optional components such as preservatives, viscosity modifiers, pH modifiers, fragrances, and the like. The selection of these minors will vary depending on the physical and chemical characteristics of the particular ingredients selected.

Hair Conditioner product

An exemplary pourable hair conditioner composition is characterized by:
  a water-based composition that contains water, from about 50% to about 96% by weight,
  a pH range from 3 to 6.5, preferably from 3 to 5.
  A composition that: (i) contains from about 0.1 to 15% by weight of one or more organic, cationic conditioning agents, (ii) contains from about 0.5 to 10% by weight of at least one or more texturing agents, (iii) may contain from about 0.01% to about 10%, by weight of the composition, of silicone, (iv) may contain other optional ingredients, for hair benefit or aesthetic properties of the product, (v) the microcapsule composition of this invention at a level of 0.01% to 5% (e.g., 0.02% to 3%, 0.05% to 2%, 0.07%, 0.2%, 0.5%, and 1%), and (vi) optionally a free fragrance that is not encapsulated at a level of 0.01% to 5% (e.g., 0.02% to 2%, 0.05% to 1%, 0.08%, 0.5%, and 1%).

Liquid Detergents

A liquid detergent is in general an easy pouring (range of viscosity from 100 to 10000 mPa·s at 21 s$^{-1}$ preferably between 1,000 and 6,000 mPa·s measured at room temperature), transparent or translucent, liquid compositions (preferably isotropic) wherein a polymer or mixture of polymers are used to suspend relatively large size particles. The pH value of the detergents is generally in the range of from 5 to 12, preferably in the range from 7 to 10.5. The liquid detergent can contain the microcapsule composition of this invention at a level of 0.01% to 5% (e.g., 0.02% to 3%, 0.05% to 2%, 0.07%, 0.2%, 0.5%, and 1%), and optionally a free fragrance that is not encapsulated at a level of 0.01% to 5% (e.g., 0.02% to 2%, 0.05% to 1%, 0.08%, 0.5%, and 1%).

An exemplary liquid detergent is a transparent or translucent aqueous solution comprising at least (to the total weight of the composition):
  a. Non-soap surfactant system comprising anionic and/or nonionic surfactants, with a range of 1 wt % to 60 wt %, preferably 15 wt % to 35 wt %
  b. Solvent which reaches 0.5 wt % to 50 wt %, preferably 10 wt % to 20 wt %
  c. One or more soil release polymer (SRP) that can be between 0.01 wt % to 10 wt %, but preferably 0.9 wt % to 2.5 wt %,
  d. Water (comprised the builder system) is present up to 85 wt %, from 1% to 45% preferably between 5 wt % to 35 wt % and more preferably between 15 wt % to 25 wt %,
  wherein the weight ratio of non-soap anionic surfactant to nonionic surfactant is at least 1.2, preferably at least 1.25; the stability of a liquid detergent is driven by the individual amount of the components and by the ratios between them. See WO2017173591A1 and EP2982735B1.

Fabric Conditioning Products

The microcapsule composition is suitable for use in fabric conditioning products.

The fabric conditioning compositions having the microcapsule composition contains at least one fabric conditioning agent, preferably at a concentration of 1% to 30% (e.g., 4% to 20%, 4% to 10%, and 8% to 15%). It would be obvious to a skilled person in the art to determine the concentration of a fabric conditioning agent while keeping its conditioning benefits and also maintaining a reasonable stability and shelf life.

Suitable fabric conditioning agents include cationic surfactants. Non-limiting examples are quaternary ammonium compounds such as alkylated quaternary ammonium compounds, ring or cyclic quaternary ammonium compounds, aromatic quaternary ammonium compounds, diquaternary ammonium compounds, alkoxylated quaternary ammonium compounds, amidoamine quaternary ammonium compounds, ester quaternary ammonium compounds, and mixtures thereof. Fabric softening compositions, and components thereof, are generally described in US 2004/0204337 and US 2003/0060390. Suitable softening agents include esterquats such as Rewoquat WE 18 commercially available from Evonik Industries and Stepantex SP-90 commercially available from Stepan Company.

The microcapsule composition can be present at a level of 0.02% to 15% (e.g., 0.05% to 10%, 0.1% to 5%, and 0.5% to 3%) so that the fabric conditioning composition has a fragrance load of 0.01% to 5% (e.g., 0.02% to 3%, 0.05% to 2%, and 0.1% to 1%).

An exemplary fabric softening product is an aqueous dispersion of quaternary ammonium compound (QAC) in which are characterized by;
 a) the viscosity of the final product ranges from 5 to 300 mPa·s@106 s$^{-1}$, preferable 20 to 150 mPa·s,
 b) the pH of the product ranges from 1.5 to 5, preferable 2 to 3,
 c) the level of QAC ranges 0.5 to 20 wt %, preferably from 1 to 16 wt %, more preferably 6 to 12 wt % softening active. The preferred, typical cationic fabric softening components include water-insoluble quaternary-ammonium fabric softeners, the most commonly used having been di-long alkyl chain ammonium chloride or methyl sulfate. Preferred cationic softeners include but not limited to the following:
 1) rapidly biodegradable quaternary ammonium compounds which contain 1 or more ester bonds situated between the quaternary-ammonium group and the long alkyl chain: (i) TEA ester quats, (ii) DEEDMAC, and (iii) HEQ,
 2) non-ester quaternary ammonium compounds: (i) ditallow dimethylammonium chloride (DTDMAC); (ii) dihydrogenated tallow dimethylammonium chloride; (iii) dihydrogenated tallow dimethylammonium methylsulfate; (iv) distearyl dimethylammonium chloride; (v) dioleyl dimethylammonium chloride; (vi) dipalmityl hydroxyethyl methylammonium chloride; (vii) stearyl benzyl dimethylammonium chloride; (viii) tallow trimethylammonium chloride; (ix) hydrogenated tallow trimethylammonium chloride; (x) C12-C14 alkyl hydroxyethyl dimethylammonium chloride; (xi) C12-18 alkyl dihydroxyethyl methylammonium chloride; (xii) di(stearoyloxyethyl) dimethylammonium chloride (DSOEDMAC); (xiii) di(tallowoyloxyethyl) dimethylammonium chloride; (xiv) ditallow imidazolinium methylsulfate; and (xv) 1-(2-tallowylamidoethyl)-2-tallowyl imidazolinium methylsulfate.

All parts, percentages and proportions refer to herein and in the claims are by weight unless otherwise indicated.

The values and dimensions disclosed herein are not to be understood as being strictly limited to the exact numerical values recited. Instead, unless otherwise specified, each such value is intended to mean both the recited value and a functionally equivalent range surrounding that value. For example, a value disclosed as "50%" is intended to mean "about 50%."

The terms "include," "includes," and "including," are meant to be non-limiting.

The terms "capsule" and "microcapsule" herein are used interchangeably.

The terms "polyfunctional isocyanate," "multifunctional isocyanate," and "polyisocyanate" are used interchangeably and refer to a compound having two or more isocyanate (—NCO) groups.

The terms "polyfunctional amine," "multifunctional amine," and "polyamine" are used interchangeably and refer to a compound containing one, two, or more primary or secondary amine groups. These terms also refers to a compound containing one or more primary/secondary amine groups and one or more hydroxyl groups (—OH).

The terms "polyethyleneimine," "polyethyleneimines," "polyethylenimine," and "polyethylenimines" are used interchangeably.

The terms "polyfunctional alcohol," "multifunctional alcohol," "poly alcohol," and "polyol" are used interchangeably and refer to a compound having two or more hydroxyl groups.

The term "degree of polymerization" refers to the number of repeat units in a polymer.

The term "degree of crosslinking" refers to percent of interconnecting units over the total repeat unit. It is generally measured by swelling experiments. See ASTM Standard Test Method ASTM D2765-11; Lange, Colloid & Polymer Science 264, 488-93 (1986).

The terms "multi-functional nucleophile" and "polyfunctional nucleophile" are used herein interchangeably. They both refer to an aliphatic or aromatic hydrocarbon onto which is attached two or more nucleophilic groups such as primary/secondary amine groups and the hydroxyl group.

The term "multi-functional electrophile" and "polyfunctional electrophile" are used interchangeably and refer to an aliphatic or aromatic hydrocarbon, onto which is attached two or more electrophilic groups reactive towards the nucleophilic group. Examples of an electrophilic group include: aldehydes, halide, sulfate esters, sulphonate esters, epoxide, chlorohydrins as well as terminal olefins conjugated with a carbonyl group including ketone, amide, or ester.

The invention is described in greater detail by the following non-limiting examples. Without further elaboration, it is believed that one skilled in the art can, based on the description herein, utilize the present invention to its fullest extent. All publications cited herein are incorporated by reference in their entirety.

Example 1

An oil phase was provided by mixing 182.8 grams ("g") of Fragrance 1 (a research fragrance accord, International Flavors & Fragrances, Union Beach, NJ), 45.7 g of caprylic/capric triglyceride (NEOBEE® oil M-5, Stepan Company, Chicago, IL), and 18.3 g of polymeric methylene phenyl diisocyanate (Lupranate® M20, BASF corporation, Wyandotte, Michigan, USA). In a separate beaker, an aqueous phase was prepared by mixing an aqueous solution (28.6 g) containing 10% polyvinyl pyrrolidone (Luviskol® K90, BASF corporation, Wyandotte, Michigan, USA) and 2.9 g of sodium salt of alkylnaphthalenesulfonate formaldehyde condensate (Morwet® D-425, Akzo Nobel, Fort Worth, Tex. USA) in 253.8 g of water. The oil phase was emulsified into the aqueous phase to form a fragrance emulsion under a shearing of 5000 rpm for three minutes. The fragrance emulsion was then heated to 35° C., to which were added 10 g of 25% sodium carbonate aqueous solution and 20.6 g of a 40% hexamethylene diamine (HMDA) (INVISTA, Wichita, Kans. USA) (aqueous solution) under constant agitation to obtain an oil-in-water emulsion. The resultant capsule slurry was cured at 55° C. for two hours. The slurry was cooled to room temperature (25° C.) and the pH was adjusted to 8 using citric acid to obtain Microcapsule Composition 1 of this invention.

In this example, Fragrance 1 was used. This fragrance contains 31.1 wt % aldehydes. The amount of each aldehyde is shown in Table 1 below.

TABLE 1

| Aldehyde | % by weight of fragrance |
|---|---|
| octanal (aldehyde C-8) 124-13-0 | 3.4 |
| nonanal (aldehyde C-9) 124-19-6 | 2.7 |
| decanal (aldehyde C-10) 112-31-2 | 5.5 |
| 2-methyl undecanal (aldehyde C-12 MNA) 110-41-8 | 1.9 |
| 2,4-ivy carbaldehyde (Ald AA triplal) 68039-49-6 | 9.7 |
| magnolia decadienal (Floral super) 71077-31-1 | 0.1 |
| alpha-hexyl cinnamaldehyde (Hexyl Cinn Ald) 101-86-0 | 6.8 |
| 3-(p-cumenyl)propionaldehyde (Cyclemax) 7775-00-0 | 1 |
| Total | 31.1 |

Comparative Composition

Comparative Composition 2a was prepared following the same procedure as described in Example 1, except that 10 g of water was added instead of the sodium carbonate aqueous solution. The composition aggregated and had a very high viscosity.

Comparative Composition 2b, 2c, and 2d were prepared following the same procedure as Comparative Composition 2a except that a different aldehyde was used. See Table 2 below.

TABLE 2

| Sample | Aldehyde | ClogP | Wt % | Encapsulation |
|---|---|---|---|---|
| 2b | 3-(p-cumenyl) propionaldehyde | 3.37 | 10% | aggregated Viscosity > 1500 |
| 2c | Octanal | 2.90 | 2.5% | Failed. Viscosity > 1500 |
| 2d | Decanal | 3.98 | 4.5% | Fail: Slurry Solidified during Synthesis |

TABLE 3

Fragrance 2

| Aldehyde | % of fragrance (w/w) |
|---|---|
| octanal (aldehyde C-8) 124-13-0 | 7.5 |
| nonanal (aldehyde C-9) 124-19-6 | 7 |
| decanal (aldehyde C-10) 112-31-2 | 11.5 |
| 2-methyl undecanal (aldehyde C-12 MNA) 110-41-8 | 3 |
| 2,4-ivy carbaldehyde (Ald AA triplal) 68039-49-6 | 14.5 |
| alpha-hexyl cinnamaldehyde (Hexyl Cinn Ald) 101-86-0 | 6.8 |
| Total | 50.3 |

Example 2

Microcapsule Composition 2 was prepared following the same procedure as described in Example 1, except that 182.8 g of Fragrance 2 was added instead of Fragrance 1. The aldehyde contents of this fragrance are shown in Table 3 above.

Example 3

Microcapsule Composition 3 was prepared following the same procedure as described in Example 1, except that 182.8 g of Fragrance 3 was added instead of Fragrance 1. The aldehyde contents of this fragrance are shown in Table 4 below.

TABLE 4

Fragrance 3

| Aldehyde | % of fragrance (w/w) |
|---|---|
| octanal (aldehyde C-8) 124-13-0 | 4 |
| decanal (aldehyde C-10) 112-31-2 | 8 |
| 2-methyl undecanal (aldehyde C-12 MNA) 110-41-8 | 1 |
| 2,4-ivy carbaldehyde (Ald AA triplal) 68039-49-6 | 2 |
| Total | 15 |

Example 4

Microcapsule Composition 4 was prepared following the same procedure as described in Example 1, except that 182.8 g of Fragrance 4 was added instead of Fragrance 1. The aldehyde contents of this fragrance are shown in Table 5 below.

TABLE 5

Fragrance 4

| Aldehyde | % of fragrance (w/w) |
|---|---|
| octanal (aldehyde C-8) 124-13-0 | 1.4 |
| nonanal (aldehyde C-9) 124-19-6 | 0.6 |
| decanal (aldehyde C-10) 112-31-2 | 3.2 |
| 2-methyl undecanal (aldehyde C-12 MNA) 110-41-8 | 2 |
| 2,4-ivy carbaldehyde (Ald AA triplal) 68039-49-6 | 2.4 |
| Total | 9.6 |

Example 5

Microcapsule Composition 5 was prepared following the same procedure as described in Example 1, except that 182.8 g of Fragrance 5 was added instead of Fragrance 1. The aldehyde contents of this fragrance are shown in Table 6 below.

TABLE 6

Fragrance 5

| Aldehyde | % of fragrance (w/w) |
|---|---|
| Ald C8 | 5.6 |
| Ald C9 | 4 |
| Ald C10 | 8 |
| Ald C12 MNA | 3 |
| Ald AA triplal | 11 |
| Dodecanal Trans-2 | 0.6 |
| Floral super | 0.15 |
| Hexyl Cinn Ald | 1.7 |
| Cyclamal | 2 |
| Total | 36.05 |

Example 6

Microcapsule Composition 6 was prepared following the same procedure as described in Example 5, except that 10 g of 25 wt % NaCl solution was used instead of the $Na_2CO_3$ solution.

Example 7

Microcapsule Composition 7 was prepared following the same procedure as described in Example 5, except that 10 g of 25 wt % $CaCl_2$ solution was used instead of the $Na_2CO_3$ solution.

Example 8

Microcapsule Composition 8 was prepared following the same procedure as described in Example 5, except that 10 g of 25 wt % $Na_2SO_4$ solution was used instead of the $Na_2CO_3$ solution.

Example 9

Microcapsule Composition 9 was prepared following the same procedure as described in Example 5, except that 10 g of 25 wt % sodium ascorbate (vitamin C or "VC") solution was used instead of the $Na_2CO_3$ solution.

Example 10

Microcapsule Composition 10 was prepared as described in Example 5, except that additional 10 g of 25 wt % VC solution was used together with the $Na_2CO_3$ solution.

Example 11

Microcapsule Composition 11 was prepared following the procedure below.

An oil phase was provided by mixing 192 g of fragrance 1 (International Flavors & Fragrances, Union Beach, NJ), 48 g of caprylic/capric triglyceride (NEOBEE® oil M-5, Stepan, Chicago, IL), and 19.2 g of trimethylol propane-adduct of xylylene diisocyanate (TAKENATE® D110-N, Mitsui Chemicals Corporation, Rye Brook, NY). In a separate beaker, an aqueous phase was prepared by mixing 30 g of 10% polyquaternium-11 aqueous solution (Luviquat® PQ-11 AT1, BASF, Ludwigshafen, Germany) in 206.2 g of water. The oil phase was emulsified into the aqueous phase to form a fragrance emulsion under a shearing of 5000 rpm for three minutes. The fragrance emulsion was heated to 35° C., to which were added 10 g of 25% sodium carbonate solution and 30.2 g of a 30% branched polyethyleneimine (Lupasol® FT WF solution, BASF, Ludwigshafen, Germany) under constant agitation. The resultant capsule slurry was cured at 55° C. for two hours. The slurry was cooled to room temperature (25° C.) and the pH was adjusted to 8 using citric acid to obtain the microcapsule composition 11 of this invention.

Evaluation: Viscosity, Free Oil, and Particle Size

The microcapsule compositions 1-11 were evaluated for their viscosity, free oil content and particle size. The results were shown in Table 7 below.

The viscosity was reported at 21 s- and measured using Automatic Rheometer (commercially available from Anton Paar, Austria).

The free oil content was analyzed using a gas chromatography.

The particle size was obtained using Master Sizer 3000 commercially available from Malvern Panalytical, UK.

TABLE 7

| Composition | Aldehyde wt % | Salt | pH | Viscosity cP | Free Oil wt % | Particle Size, μm |
|---|---|---|---|---|---|---|
| 1 | 31.1 | $Na_2CO_3$ | 10 | 285 | 0.5 | 11 |
| Comparative | 31.1 | No salt | 5 | 3003 | 0.4 | 92 |
| 2 | 50.3 | $Na_2CO_3$ | 10 | 927 | 0.6 | 23 |
| 3 | 15 | $Na_2CO_3$ | 10 | 946 | 0.5 | 25 |
| 4 | 9.6 | $Na_2CO_3$ | 10 | 390 | 0.2 | 10 |
| 5 | 36.05 | $Na_2CO_3$ | 10 | 590 | 0.4 | 16 |
| 6 | 36.05 | NaCl | 5 | 829 | 0.4 | 20 |
| 7 | 36.05 | $CaCl_2$ | 9 | 755 |  | 16 |
| 8 | 36.05 | $Na_2SO_4$ | 5 | 685 | 0.5 | 18 |
| 9 | 36.05 | VC | 5 | 874 | 0.8 | 22 |
| 10 | 36.05 | VC + $Na_2CO_3$ | 10 | 561 | 1 | 18 |
| 11 | 31.1 | $Na_2CO_3$ | 10 | 1170 | 0.83 | 33 |

Example 12

Microcapsule composition 12 was prepared following the procedure below. An oil phase was provided by mixing 216 g of Fragrance 12 containing 9% aldehydes (International Flavors & Fragrances, Union Beach, NJ), 54 g of caprylic/capric triglyceride (NEOBEE® oil M-5, Stepan, Chicago, IL), and 12 g of trimethylol propane-adduct of xylylene diisocyanate (TAKENATE® D110-N, Mitsui Chemicals Corporation, Rye Brook, NY). In a separate beaker, an aqueous phase was prepared by mixing (i) 1.8 g of solid sodium chloride, (ii) an aqueous solution (30 g) containing 10 wt % of polyvinyl pyrrolidone (Luviskol® K90, BASF corporation, Wyandotte, Michigan, USA), and (ii) an aqueous solution (60 g) of 20 wt % solution Polyquaternium-11 (Luviquat® PQ-11 AT1, BASF, Ludwigshafen, Germany) in 200.4 g of water. The oil phase was emulsified into the aqueous phase to form a fragrance emulsion under a shearing of 9500 rpm for three minutes. The fragrance emulsion was heated to 25° C., to which was added 30 g of a 30 wt % branched polyethylenimine aqueous solution (Lupasol® WF, commercially available from BASF, Florham Park, NJ) under constant agitation. The resultant capsule slurry was cured at 55° C. for two hours to obtain Microcapsule Composition 12.

Example 13

Microcapsule Composition 13 was prepared following the same procedure as described in Example 12, except that 5.4 g of solid sodium chloride was used instead of 1.8 g.

Example 14

Microcapsule Composition 14 was prepared following the same procedure as described in Example 12, except 9 g of solid sodium chloride was used instead of 1.8 g.

Example 15

Microcapsule Composition 15 was prepared following the same procedure as described in Example 12, except 9 g of solid calcium chloride was used instead of sodium chloride.

Example 16

Microcapsule Composition 16 was prepared following the same procedure as described in Example 12, except 3.6 g of solid sulfate was used instead of sodium chloride. Comparative composition 17

Comparative Composition 17 was prepared following the same procedure as described in Example 14, except that no sodium chloride was used.

Viscosity of Microcapsule Compositions 12-16 and Comparative Composition 17

The viscosity was measured following the procedure described above. The results are shown in Table 8 below.

TABLE 8

| Composition | Salt | Viscosity (cP) |
|---|---|---|
| Comparative 17 | Control no salt | 3433 |
| 12 | 0.3% NaCl | 1647 |
| 13 | 0.9% NaCl | 1240 |
| 14 | 1.5% NaCl | 1107 |
| 15 | 1.5% CaCl$_2$ | 1247 |
| 16 | 0.6% Na$_2$SO$_4$ | 1500 |

Example 18

Microcapsule Composition 18 was prepared following the same procedure as described in Example 1, except using 28.6 g of a 10% (w/v) solution containing polyvinyl pyrrolidone with a molecule weight of 30000 Daltons (Luviskol® K30, BASF) instead of a polyvinyl pyrrolidone with a molecular weight of 90000 Daltons (Luviskol® K90).

Examples 19 and 20

Microcapsule Compositions 19 and 20 were prepared by mixing Microcapsule Composition 18 with a copolymer of acrylic acid and acrylate (Aculyn™ 33A, Dow Chemical Company, Midland, Michigan). The copolymer of acrylic acid and acrylate was added at a level of 3% by weight of the microcapsule composition. Their pH was adjusted using citric acid, either before or after the addition of the copolymer. Microcapsule Composition 19 had a final pH of 8 and Microcapsule Composition 20 had a final pH of 6.5-7.5. Microcapsule Compositions 19 and 20 had an acceptable viscosity between 234 mPa·s and 1290 mPa·s measured at 21 s$^{-1}$.

Example 21

Microcapsule Composition 21 was prepared following a similar procedure with the agents showing in Table 9 below. After the microcapsule slurry was cooled to 25° C., a cationic acrylic acid polymer (12 g, Flosoft™ FS-222, SNF Andrézieux France) was added to obtain Microcapsule Composition 21.

TABLE 9

Microcapsule Composition 21
Shearing 9500 RPM, Curing 55° C., 2 hours

| | Amount, g | wt %[a] |
|---|---|---|
| Microcapsule Core | | |
| Fragrance 1[b] | 192 | 32% |
| caprylic/capric triglyceride[c] | 48 | 8% |
| Microcapsule Wall | | |
| polyisocyanate[d] | 9.5 | 1.58% |
| HMDA[e] | 4.28 | 0.71% |
| PVP[f] | 3 | 0.5% |
| PQ-118[g] | 6 | 1% |
| PQ-6[h] | 6 | 1% |
| Sodium sulfate | 2.5 | 0.42% |
| Flosoft FS-222 | 12 | 2% |
| Water | 316.72 | 52.79% |
| Total | 600 | 100% |

[a] by weight of the microcapsule composition
[b] Fragrance containing 31.1% of aldehyde ingredients
[c] NEOBEE ® oil M-5 from Stepan Company
[d] polymeric methylene diphenyl diisocyanate, Lupranate ® M20 from BASF
[e] Hexamethylene diamine from Invista
[f] Polyvinyl pyrrolidone, Luviskol ® K90 from BASF
[g] Polyquaternium-11, Luviquat ® PQ-11 AT 1 from BASF
[h] Polyquaternium-6, Merquat™ 100 from Nalco
[i] Flosoft™ FS-222 from SNF

Example 22

Microcapsule Composition 22 was prepared following a similar procedure as Example 21 using Fragrance 6 and other agents showing in Table 10 below. Fragrance 6 had 8.1% of aldehydes as shown in Table 11.

TABLE 10

Microcapsule Composition 22
Shearing 5000 RPM, Curing 55° C., 2 hours

| | Amount, g | wt %[a] |
|---|---|---|
| Microcapsule Core | | |
| Fragrance 6[b] | 172.6 | 28.77 |
| caprylic/capric triglyceride[c] | 43.2 | 7.2 |
| Microcapsule Wall | | |
| polyisocyanate[d] | 17.4 | 2.9 |
| HMDA[e] | 3.92 | 0.65 |
| alkylnaphthalenesulfonate formaldehyde condensate[f] | 2.7 | 0.45 |
| PVP[g] | 1.43 | 0.24 |
| Crosslinked polyacrylic acid[h] | 1.2 | 0.2 |
| Sodium sulfate | 2.4 | 0.4 |
| Water | 355.15 | 59.19 |
| Total | 600 | 100% |

[a] by weight of the microcapsule composition
[b] Fragrance containing 8.1% of aldehyde ingredients
[c] NEOBEE ® oil M-5 from Stepan Company
[d] polymeric methylene diphenyl diisocyanate, Lupranate ® M20 from BASF
[e] Hexamethylene diamine from Invista
[f] Morwet ® D-425 from Akzo Nobel
[g] Polyvinyl pyrrolidone, Luviskol ® K90 from BASF
[h] Carbopol ® ETD 2050 from Lubrizol, Wickliffe, Ohio

TABLE 11

| Fragrance 6 | |
| --- | --- |
| Aldehyde | Wt % |
| Cyclamal | 2.6% |
| Trifernal | 0.5% |
| ALD AA Triplal | 2.4% |
| Melonal | 2.1% |
| Cyclemax | 0.5% |
| Total | 8.1% |

COMPARATIVE COMPOSITIONS 22A' and 22B'

Comparative Compositions 22A' and 22B' were prepared following a similar procedure as Microcapsule Composition 22 using the agents showing in Tables 12 and 13 below. Both Comparative Compositions 22A' and 22B' were lumpy viscous slurries with a viscosity greater than 6000 mPa·s. Both compositions were not suitable for use due to their high viscosity.

TABLE 12

Comparative Composition 22A'
Shearing 5000 RPM, Curing 55° C., 2 hours

| | Amount, g | wt %$^a$ |
| --- | --- | --- |
| Microcapsule Core | | |
| Fragrance 2$^b$ | 172.6 | 28.77 |
| caprylic/capric triglyceride$^c$ | 43.2 | 7.2 |
| Microcapsule Wall | | |
| polyisocyanate$^d$ | 17.4 | 2.9 |
| HMDA$^e$ | 3.92 | 0.65 |
| sodium salt of alkylnaphthalenesulfonate formaldehyde condensate$^f$ | 2.7 | 0.45 |
| Crosslinked polyacrylic acid$^g$ | 1.2 | 0.2 |
| Water | 358.98 | 59.83 |
| Total | 600 | 100% |

$^a$by weight of the microcapsule composition
$^b$Fragrance containing 8.1% of aldehyde ingredients
$^c$NEOBEE ® oil M-5 from Stepan Company
$^d$polymeric methylene diphenyl diisocyanate, Lupranate ® M20 from BASF
$^e$Hexamethylene diamine from Invista
$^f$Morwet ® D-425 from Akzo Nobel
$^g$Carbopol ® ETD 2050 from Lubrizol, Wickliffe, Ohio

TABLE 13

Comparative Composition 22B'
Shearing 5000 RPM, Curing 55° C., 2 hours

| | Amount, g | wt %$^a$ |
| --- | --- | --- |
| Microcapsule Core | | |
| Fragrance 2$^b$ | 172.6 | 28.77 |
| caprylic/capric triglyceride$^c$ | 43.2 | 7.2 |
| Microcapsule Wall | | |
| polyisocyanate$^d$ | 17.4 | 2.9 |
| HMDA$^e$ | 3.92 | 0.65 |
| alkylnaphthalenesulfonate formaldehyde condensate$^f$ | 2.7 | 0.45 |
| PVP$^g$ | 1.43 | 0.24 |
| Crosslinked polyacrylic acid$^h$ | 1.2 | 0.2 |
| Water | 357.55 | 59.59 |
| Total | 600 | 100% |

$^a$by weight of the microcapsule composition
$^b$Fragrance containing 8.1% of aldehyde ingredients
$^c$NEOBEER ® oil M-5 from Stepan Company
$^d$polymeric methylene diphenyl diisocyanate, Lupranate ® M20 from BASF
$^e$Hexamethylene diamine from Invista
$^f$Morwet ® D-425 from Akzo Nobel
$^g$Polyvinyl pyrrolidone, Luviskol ® K90 from BASF
$^h$Carbopol ® ETD 2050 from Lubrizol, Wickliffe, Ohio

Example 23

Microcapsule Composition 23 was prepared following a similar procedure as Example 21 using Fragrance 6 and other agents showing in Table 14 below.

Comparative Composition 23'

Comparative Composition 23' was prepared following a similar procedure as Example 23 using the agents showing in Table 15 below. Comparative Compositions 23' was a lumpy viscous slurry with a viscosity greater than 6000 mPa·s. This composition was not suitable for use due to its high viscosity.

TABLE 14

Microcapsule Composition 23
Shearing 13500 RPM, Curing 55° C., 2 hours

| | Amount, g | wt %$^a$ |
| --- | --- | --- |
| Microcapsule Core | | |
| Fragrance 3$^b$ | 192 | 32 |
| caprylic/capric triglyceride$^c$ | 48 | 8 |
| Microcapsule Wall | | |
| polyisocyanate$^d$ | 19.2 | 3.2 |
| BPEI$^e$ | 15.1 | 2.52 |
| PVP$^f$ | 3 | 0.5 |
| PQ-11$^g$ | 12 | 2 |
| Sodium carbonate | 1.5 | 0.25 |
| Water | 309.2 | 51.53 |
| Total | 600 | 100% |

$^a$by weight of the microcapsule composition
$^b$Fragrance containing 2.8% of aldehyde ingredients
$^c$NEOBEE ® oil M-5 from Stepan Company
$^d$Trimethylol propane-adduct of xylylenediisocyanate, Takente™ D110-N from Mitsui Chemicals
$^e$Branched polyethyleneimine, Lupasol ® FT WF from BASF
$^f$Polyvinyl pyrrolidone, Luviskol ® K90 from BASF
$^g$Polyquaternium-11, Luviquat ® PQ-11 AT 1 from BASF

TABLE 15

Microcapsule Composition 23'
Shearing 9500 RPM, Curing 55° C., 2 hours

|  | Amount, g | wt %[a] |
|---|---|---|
| Microcapsule Core |  |  |
| Fragrance 2[b] | 192 | 32 |
| caprylic/capric triglyceride[c] | 48 | 8 |
| Microcapsule Wall |  |  |
| polyisocyanate[d] | 19.2 | 3.2 |
| BPEI[e] | 15.1 | 2.52 |
| CMC[f] | 0.6 | 0.1 |
| Sodium polystyrene sulfonate[g] | 3 | 0.5 |
| Water | 322.1 | 53.68 |
| Total | 600 | 100% |

[a]by weight of the microcapsule composition
[b]Fragrance containing 8.1% of aldehyde ingredients
[c]NEOBEE ® oil M-5 from Stepan Company
[d]polymeric methylene diphenyl diisocyanate, Lupranate ® M20 from BASF
[e]Branched polyethyleneimine, Lupasol ® FT WF from BASF
[f]Carboxymethyl cellulose, Walocel™ 50K from Dow Chemical
[g]Flexan ® II, from AkzoNobel Fabric Conditioners Microcapsule compositions described above were incorporated into a fabric conditioner base at a neat oil equivalence from 0.05 wt % to 0.8 wt % relative to the weight of the final product. As an illustration, 100 g of a final fabric conditioner (0.3% NOE) was prepared by adding 0.968 g of a microcapsule composition and 9.032 g of water into 90 g of a fabric conditioner base. The microcapsule compositions were easily dispersed without any agglomeration, flocculation, or sedimentation from the first day of incorporation to many months at 37° C.

Shampoos and Hair Conditioners

Microcapsule Compositions 21-23 were incorporated into an unperfumed shampoo base and an unperfumed hair conditioner base to obtain a shampoo product and a hair conditioner product.

Both the shampoo product and the hair conditioner product were used to treat hair swatches following a standard protocol. The deposition of the microcapsule onto the hair was analyzed using a GC-MS method.

Unexpectedly, the microcapsule compositions of this invention had a high deposition.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Indeed, to achieve the purpose of deliver an active material, one skilled in the art can design and prepare a capsule composition by using different encapsulating polymers, coatings, polyfunctional nucleophiles and/or electrophiles, and/or capsule formation aids, varying the concentrations of these wall-forming materials and/or catalysts to achieve desirable organoleptic or release profiles in a consumable product. Further, the ratios among polyfunctional nucleophiles and/or electrophiles, capsule forming aids, adjuvants, core modifiers, active materials, and catalysts can also be determined by a skilled artisan through assays known in the art to prepare capsule compositions with desirable properties.

From the above description, a skilled artisan can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A microcapsule composition comprising a plurality of microcapsules dispersed in an aqueous phase,
   wherein
      each microcapsule having a microcapsule core and a microcapsule wall encapsulating the microcapsule core,
      the microcapsule core contains a fragrance having 8% to 100% one or more aldehydes by weight of the fragrance,
      the microcapsule wall is formed of an encapsulating polymer,
      the encapsulating polymer contains a polyurea polymer that is a reaction product of a multi-functional electrophile and a multi-functional nucleophile,
      the multi-functional electrophile contains a polyisocyanate,
      the multi-functional nucleophile contains a polyamine,
      the microcapsule composition has a viscosity of 2000 centipoises or less at a shear rate of 21 hertz and a temperature of 25° C., and
      the microcapsule composition contains by weight (i) 5% to 80% of the fragrance in the microcapsule core, (ii) 0.1% to 15% of the encapsulating polymer, and (iii) at least 0.01% of a water-soluble inorganic or organic salt of an alkali or alkaline earth metal.

2. The microcapsule composition of claim 1, wherein the microcapsule composition contains by weight 10% to 60% of the microcapsule and 2% to 30% of the one or more aldehydes, and each of the one or more aldehydes either (i) has a C log P of 4 or less or (ii) lacks a substitution on the alpha and beta carbon position relative to any aldehyde function group on the one or more aldehydes.

3. The microcapsule composition of claim 1, further comprising a dispersant at a level of 0.1% to 10% by weight of the composition.

4. The microcapsule composition of claim 3, wherein the dispersant contains polyvinylpyrrolidone at a level of 0.2% to 5% by weight of the composition.

5. The microcapsule composition of claim 3, wherein the dispersant contains a polyvinyl alcohol, polystyrene sulfonate, carboxymethyl cellulose, naphthalene sulfonate condensate salt, polyvinylpyrrolidone, copolymer of vinyl pyrrolidone and quaternized dimethylaminoethyl methacrylate, or combination thereof.

6. The microcapsule composition of claim 1, wherein the water-soluble organic or inorganic salt of an alkali metal or alkaline earth metal is selected from the group consisting of sodium chloride, sodium sulfate, sodium carbonate, sodium bicarbonate, cesium carbonate, potassium chloride, potassium sulfate, potassium carbonate, potassium bicarbonate, lithium chloride, lithium sulfate, sodium ascorbate, sodium acetate, sodium benzoate, calcium chloride, and combinations thereof.

7. The microcapsule composition of claim 1, wherein microcapsule has a size of 0.1 to 1000 microns; the polyisocyanate is a trimer of hexamethylene diisocyanate, a trimer of isophorone diisocyanate, a biuret of hexamethylene diisocyanate, a polyisocyanurate of toluene diisocyanate, a trimethylol propane-adduct of toluene diisocyanate, a trimethylol propane-adduct of xylylene diisocyanate, or a combination thereof, and the polyamine is hexamethylenediamine, branched polyethyleneimine, ethylenediamine, 1,3-diaminopropane, 1,4-diaminobutane, diethylenetriamine, pentaethylenehexamine, bis(3-aminopropyl)amine, bis(hexanethylene)triamine, tris(2-aminoethyl)amine, triethylenetetramine, N,N'-bis(3-aminopropyl)-1,3-propanediamine, tetraethylenepentamine, pentaethylenehexamine, chitosan, nisin, gelatin, 1,3-diamino-guanidine, 1,1-dimethylbiguanide, guanidine, arginine, lysine, ornithine, or a combination thereof.

8. The microcapsule composition of claim 1, further comprising a free fragrance oil or a second delivery system.

9. The microcapsule composition of claim 1, further comprising a deposition aid selected from the group consisting of polyquaternium-4, polyquaternium-5, polyquaternium-6, polyquaternium-7, polyquaternium-10, polyquaternium-11, polyquaternium-16, polyquaternium-22, polyquaternium-24, polyquaternium-28, polyquaternium-37, polyquaternium-39, polyquaternium-44, polyquaternium-46, polyquaternium-47, polyquaternium-53, polyquaternium-55, polyquaternium-67, polyquaternium-68, polyquaternium-69, polyquaternium-73, polyquaternium-74, polyquaternium-77, polyquaternium-78, polyquaternium-79, polyquaternium-79/hydrolyzed keratin, polyquaternium-80, polyquaternium-81, polyquaternium-82, polyquaternium-86, polyquaternium-88, polyquaternium-101, polyvinylamine, polyethyleneimine, a copolymer of vinylamine and vinylformamide, methacrylamidopropyl trimethyl ammonium polymer, polyacrylamide, polyacrylic acid, dimethyl ammonium polymer, polyvinylformamide, polyvinylpyrollidone, polyvinylalcohol, a copolymer of acrylamide and 3-methacryloylaminopropyl trimethylammonium, a 3-acrylamidopropyl trimethylammonium polymer or its copolymer, a diallyldimethylammoniumchloride polymer and its copolymer, a polysaccharide with saccharide unit functionalized with hydroxypropyl trimmonium, ethyltrimonium chloride methacrylate/hydrolyzed wheat protein copolymer, alkyl-monium hydroxypropyl hydrolyzed protein, xylose, galactose, hydroxypropylated glucose, hydroxyethylated glucose, hydroxymethylated glucose, functionalized branched polyethylenimine, caprolactone, catechol, hydroxypropylcellulose, polymer comprising units derived from polyethylene glycol and terephthalate, and combinations thereof.

10. The microcapsule composition of claim 1, further comprising a rheology modifier, a core modifier, or both, the rheology modifier is an alkali swellable emulsion (ASE), hydrophobically modified alkali swellable emulsion (HASE), hydrophobically modified ethoxylated urethane resin (HEUR), an acrylate copolymer, a cationic acrylamide copolymer, a polysaccharide, or cross-linked polyacrylic acid, and the core modifier is a $C_3$-$C_{40}$ ester, isopropyl myristate, $C_5$-$C_{50}$ triglyceride, D-limonene, silicone oil, mineral oil, isopropyl palmitate, isoparaffinic hydrocarbon, methyl hydrogenated rosinate, dioctyl adipate, benzyl benzoate, benzyl salicylate, triethyl citrate, or a combination thereof.

11. A method of preparing a microcapsule composition of claim 1, the method comprising:
(a) providing an oil-in-water emulsion containing (i) an aqueous phase having a microcapsule formation aid, a polyamine, a water-soluble inorganic or organic salt of an alkali or alkaline earth metal, and water, and (ii) an oil phase having the fragrance and the polyisocyanate,
(b) causing the formation of a microcapsule precursor having a microcapsule core that contains the fragrance and a microcapsule wall formed of reaction product of the polyisocyanate and polyamine, and
(c) curing the microcapsule precursor to obtain the microcapsule composition of claim 1 as a microcapsule slurry.

12. The method of claim 11, wherein the oil-in-water emulsion is prepared by the step of:
(a) providing an oil mixture containing the fragrance and the polyisocyanate,
(b) providing an aqueous solution containing the capsule formation aid,
(c) emulsifying the oil mixture into the aqueous solution to provide a preliminary emulsion,
(d) adding the water-soluble inorganic or organic salt and the polyamine to the preliminary emulsion to obtain the oil-in-water emulsion.

13. The method of claim 12, wherein the water-soluble inorganic or organic salt is added before the addition of the polyamine or is added the same time as the polyamine.

14. The method of claim 11, further comprising: removing water from the microcapsule slurry to obtain the microcapsule composition in a dry form, and optionally adding a dry flow aid to the microcapsule composition.

15. The method of claim 14, wherein the drying step is achieved through spray drying, heat drying, belt drying, filtration, centrifugation, or a combination thereof.

16. A microcapsule composition prepared by the method of claim 11.

17. A consumer product comprising the microcapsule composition of claim 1.

18. The consumer product of claim 17, wherein the consumer product is selected from the group consisting of: a baby care product, a diaper rash cream or balm, a baby powder, a diaper, a bib, a baby wipe, a cosmetic preparation, a powder foundation, a liquid foundation, an eye shadow, a lipstick or lip balm, a home care product, an all-purpose cleaner, a bathroom cleaner, a floor cleaner, a window cleaner, a plastics polish, a bleach, a toilet cleaner, a toilet rimblock, a bath tissue, a paper towel, a disposable wipe, liquid air freshener, air freshener spray, a spray dispenser product, an incense stick, a rug deodorizer, a candle, a room deodorizer, a liquid dish detergent, an automatic dish detergent, a powder dish detergent, a leather detergent, a tablet dish detergent, a paste dish detergent, a unit dose tablet or capsule, a health care device, a tampon, a feminine napkin, an anti-inflammatory balm, an anti-inflammatory ointment, an anti-inflammatory spray, a disinfectant, a personal care product, a soap, a bar soap, a liquid soap, a bath fragrance, a body wash, a non-aerosol body spray, a body milk, a cleanser, a body cream, a hand sanitizer, a hand wash, a functional product base, a sunscreen lotion, a sunscreen spray, a deodorant, an anti-perspirant, an roll-on product, an aerosol product, a natural spray product, a wax-based deodorant, a glycol type deodorant, a soap type deodorant, a facial lotion, a body lotion, a hand lotion, a miscellaneous lotion, a body powder, a shave cream, a shave gel, a shave butter, a bath soak, a shower gel, an exfoliating scrub, a foot cream, a facial tissue, a cleansing wipe, a talc product, a hair care product, a hair care with ammonia, a shampoo, a hair conditioner, a hair rinse, a hair refresher, a hair fixative or styling aid, a hair bleach, a hair dye or colorant, a fabric care product, a fabric softener, a liquid fabric softener, a fabric softener sheet, a drier sheet, a fabric refresher, an ironing water, a detergent, a laundry detergent, a liquid laundry detergent, a powder laundry detergent, a tablet laundry detergent, a laundry detergent bar, a laundry detergent cream, a hand wash laundry detergent, a scent booster, a fragrance, a cologne, compounds, an encapsulated fragrance, a fine fragrance, a men's fine fragrance, a women's fine fragrance, a perfume, a solid perfume, an Eau De Toilette product, a natural spray product, a perfume spray product, an insect repellent product, and a wildlife scent.

19. A method of imparting a cleanness and freshness sensation to a fabric product or a hair care product, the method comprising the step applying the microcapsule composition of claim 1 to the fabric product or hair care product.

20. The method of claim 19, wherein the microcapsule composition is incorporated in a fabric detergent, a fabric conditioner, a dryer sheet, a scent booster, a shampoo, or a hair conditioner.

21. The method of claim 11, wherein the water-soluble organic or inorganic salt of an alkali metal or alkaline earth metal is selected from the group consisting of sodium chloride, sodium sulfate, sodium carbonate, sodium bicarbonate, cesium carbonate, potassium chloride, potassium sulfate, potassium carbonate, potassium bicarbonate, lithium chloride, lithium sulfate, sodium ascorbate, sodium acetate, sodium benzoate, calcium chloride, and combinations thereof.

* * * * *